United States Patent
Tailor et al.

(10) Patent No.: US 8,554,305 B2
(45) Date of Patent: Oct. 8, 2013

(54) METHOD AND APPARATUS FOR PROVIDING PULSES INHALATION OF $^{17}O_2$ FOR MAGNETIC RESONANCE IMAGING OF CEREBRAL METABOLISM

(75) Inventors: Dharmesh R. Tailor, Voorhees, NJ (US); James E. Baumgardner, Folsom, PA (US); Ravinder Reddy, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 620 days.

(21) Appl. No.: 12/669,854

(22) PCT Filed: Jul. 18, 2008

(86) PCT No.: PCT/US2008/070411
§ 371 (c)(1),
(2), (4) Date: Jun. 22, 2010

(87) PCT Pub. No.: WO2009/014998
PCT Pub. Date: Jan. 29, 2009

(65) Prior Publication Data
US 2010/0282258 A1    Nov. 11, 2010

Related U.S. Application Data

(60) Provisional application No. 60/951,118, filed on Jul. 20, 2007.

(51) Int. Cl.
*A61B 5/055*   (2006.01)
*A61M 16/00*   (2006.01)
*A62B 7/00*    (2006.01)

(52) U.S. Cl.
USPC ..................................... 600/420; 128/204.18

(58) Field of Classification Search
USPC ............. 128/202.13, 202.16, 203.25, 204.23, 128/205.19; 600/419–420
See application file for complete search history.

(56) References Cited

U.S. PATENT DOCUMENTS 4,176,666 A * 12/1979 Hovey ....................... 128/205.24
4,448,192 A *  5/1984 Stawitcke et al. ........ 128/204.26
(Continued)

FOREIGN PATENT DOCUMENTS

WO    WO 2009/014998    1/2009

OTHER PUBLICATIONS

Hedlund et al, "MR-compatible ventilator for small animals: computer-controlled ventilation for proton and noble gas imaging," Magnetic Resonance Imaging, (2000) 18:753-759.*

(Continued)

*Primary Examiner* — Justine Yu
*Assistant Examiner* — Douglas Sul
(74) *Attorney, Agent, or Firm* — Woodcock Washburn, LLP

(57) ABSTRACT

Prior approaches have delivered $^{17}O_2$ to a subject by inhalation, but the relationship between local signal changes and metabolism has been complicated by $H_2^{17}O$ created in non-cerebral tissues. During a brief pulse of $^{17}O_2$ inhalation, this arterial input function for $H_2^{17}O$ is negligible due to convective transport delays. Additional delays in the arterial input function due to restricted diffusion of water makes pulsed inhalation of $^{17}O_2$ even more effective. Accordingly, ventilator system are provided to deliver $^{17}O_2$ as a brief pulse to a subject. Subsequent MR imaging demonstrates delayed appearance of $H_2^{17}O$ in the cerebral ventricles, suggesting that the arterial input function of $H_2^{17}O$ is delayed by restricted water diffusion in addition to convective transit delays. Delivery as a brief pulse therefore offers significant advantages in relating MR signal changes directly to metabolism.

12 Claims, 6 Drawing Sheets

(56) References Cited

U.S. PATENT DOCUMENTS

| | | | |
|---|---|---|---|
| 5,694,934 A | 12/1997 | Edelman | |
| 6,280,383 B1 | 8/2001 | Damadian | |
| 6,727,697 B2 | 4/2004 | Fiat | |
| 7,669,594 B2 * | 3/2010 | Downie | 128/203.12 |
| 2007/0044805 A1 | 3/2007 | Wedler et al. | |

OTHER PUBLICATIONS

Tailor, D.R. et al. "Proton MRI of metabolically produced H2170 using an efficient 17O2 delivery system," NeuroImage (2004), 22:611-618.*

Tailor, D.R. "Indirect 17O-Magnetic Resonance Imaging of Cerebral Blood Flow and Oxidative Metabolism," Diss. Univ. Penn., 2002. Ann Arbor: ProQuest, 2003.*

Agre et al., "Towards a molecular understanding of water homeostasis in the brain", Neuroscience, Nov. 2004, 129(4), 849-850.

Arai et al., "Cerebral oxygen utilization analyzed by the use of oxygen-17 and its nuclear magnetic resonance", Biochem. Biophys. Res. Commun., May 31, 1990, 169(1),153-158.

Arai et al., "In vivo oxygen-17 nuclear magnetic resonance for the estimation of cerebral blood flow and oxygen consumption", Biochem. Biophys. Res. Commun., Sep. 16, 1991, 179(2), 954-961.

Borthakur et al., "In Vivo Assessment of Human Lumbar Disc Degeneration", Proceedings 14th Scientific Meeting, International Society for Magnetic Resonance in Medicine, Seattle, May 6-12, 2006, 17-19.

Baumgardner et al., "Micropore membrane inlet mass spectrometer probes suitable for measurement of tissue surface gas tensions", J. Mass Spectrom., Apr. 1995, 30(4), 563-571.

Baumgardner et al., "Sequential $V_A/Q$ distributions in the normal rabbit by micropore membrane inlet mass spectrometry", J. Appl. Physiol., Nov. 2000, 89(5), 1699-1708.

Bentley et al., "Temperature dependence of oxygen diffusion and consumption in mammalian striated muscle", Am. J. Physiol., Jun. 1993, 264(6 pt 2), H1825-H1830.

Bitterman et al., "A micromethod for measuring carbonic anhydrase activity using 18O exchange between CO2 and H2O", J. Appl Physiol, Nov. 1988, 65(4), 1902-1906.

Borthakur et al., "A pulse sequence for rapid in vivo spin-locked MRI", J. Magn. Reson. Imaging, Apr. 2006, 23(4), 591-596.

Borthakur et al., "Three-dimensional T1ρ-weighted MRI at 1.5 Tesla", J. Magn. Reson. Imaging, Jun. 2003, 17(6), 730-736.

Brancato et al., "Iris fluorescein angiography in clinical practice", Survey Ophthalm, Jul.-Aug. 1997, 42(1), 41-70.

Bulte et al., "Measurement of cerebral blood volume in humans using hyper oxic MRI contrast", J. Magn Reson Imaging, Oct. 2007, 26(4), 894-899.

Calamita et al., "The inner mitochondrial membrane has aquaporin-8 water channels and is highly permeable to water", J. Biol. Chem., Apr. 29, 2005, 280(17), 17149-17153.

Charagundla et al., "Off-resonance proton T1ρ dispersion imaging of 17O-enriched tissue phantoms", Magn Reson Med, Apr. 1998, 39(4), 588-595.

Chiarelli et al., "A calibration method for quantitative BOLD MRI based on hyperoxia", Neuroimage, Sep. 1, 2007, 37(3), 808-820.

Ehrlich et al., "Effect of hypothermia on cerebral blood flow and metabolism in the pig", Ann Thorac Surg, Jan. 2002, 73(1), 191-197.

Fiat et al., "17O magnetic resonance imaging of the human brain", Neurol. Res., Dec. 2004, 26(8), 803-808.

Fiat et al., "Determination of the rate of cerebral oxygen consumption and regional cerebral blood flow by non-invasive 17O in vivo NMR spectroscopy and magnetic resonance imaging: Part 1. Theory and data analysis methods", Neurol Res, Sep. 1992, 14(4), 303-311.

Fiat et al., "Determination of the rate of cerebral oxygen consumption and regional cerebral blood flow by non-invasive 17O in vivo NMR spectroscopy and magnetic resonance imaging. Part 2. Determination of CMRO2 for the rat by 17O NMR, and CMRO2, rCBF and the partition coefficient for the cat by 17O MRI", Neurol. Res., Feb. 1993, 15, 7-22.

Fowler, "Lung function studies. II. The respiratory dead space", Am. J. Physiol., Jun. 1948, 154(3), 405-416.

Herscovitch et al., "What is the correct value for the brain—blood partition coefficient for water?", J. Cereb Blood Flow Metab, Mar. 1985, 5(I), 65-69.

Hlastala, "A model of fluctuating alveolar gas exchange during the respiratory cycle", Respir. Physiol., Jun. 1972, 15(2), 214-232.

Hopkins et al., "Improved sensitivity of proton MR to oxygen-17 as a contrast agent using fast imaging: detection in brain", Magn. Res. Med., Jun. 1988, 7(2), 222-229.

Hopkins et al., "Oxygen-17 compounds as potential NMR T2 contrast agents: enrichment effects of H2(17)O on protein solutions and living tissues", Magn. Res. Med., Apr. 1987, 4(4), 399-403.

Huygen et al., "Design and validation of an indicator gas injector for multiple gas washout tests in mechanically ventilated patients", Crit. Care Med., Jul. 1990, 18(7), 754-759.

Ichord et al., "Age-related differences in recovery of blood flow and metabolism after cerebral ischemia in swine", Stroke, Jan. 1991, 22(5), 626-634.

Kety et al., "The Nitrous Oxide Method for the Quantitative Determination of Cerebral Blood Flow in Man: Theory, Procedure and Normal Values", J. Clin. Invest., Jul. 1948, 27(4), 476-483.

LaManna et al., "Structural and functional adaptation to hypoxia in the rat brain", J. Exp. Biol., Aug. 2004, 207(pt 18), 3163-3169.

Lin et al., "A model of time-varying gas exchange in the human lung during a respiratory cycle at rest", Respir. Physiol., Jan. 1973, 17(1), 93-112.

Ludwigs et al., "A comparison of pressure- and volume-controlled ventilation at different inspiratory to expiratory ratios", Acta. Anaesthesiol. Scand., Jan. 1997, 41(1 pt 1), 71-77.

McKirnan et al., "Validation of a respiratory mask for measuring gas exchange in exercising swine", J. Appl Physiol, Sep. 1986, 61(3), 1226-1229.

Meiboom, "Nuclear Magnetic Resonance Study of Proton Transfer in Water", Journal of Chemical Physics, Feb. 1961, 34(2), 375-388.

Meldrum et al., "Carbonic Anhydrase, Its preparation and properties", J. Physiol, Dec. 5, 1933, 80(2), 113-142.

Mellon et al., "Single Shot T1ρ Magnetic Resonance Imaging of Metabolically Generated Water In Vivo", Advances in Experimental Medicine and Biology, Oxygen Transport to Tissue XXX, (no month available) 2009, 1, 645, 279-286.

Meyer et al., "Estimation of cerebral oxygen utilization rate by single-bolus 15O2 inhalation and dynamic positron emission tomography", J. Cereb Blood Flow Metab, Nov. 1987, 7(4), 403-414.

Mills et al., "The Kinetics of Isotopic Exchange between Carbon Dioxide, Bicarbonate Ion, Carbonate Ion and Water", J. Am Chem Soc, May 1940, 62(5), 1019-1026.

Mintun et al., "Brain oxygen utilization measured with 0-15 radiotracers and positron emission tomography", J. Nucl Med, Feb. 1984, 25(2), 177-187.

Mutoh et al., "Volume infusion produces abdominal distension, lung compression, and chest wall stiffening in pigs", J. Appl Physiol, Feb. 1992, 72(2), 575-582.

Nedergaard et al., "Dynamics of interstitial and intracellular pH in evolving brain infarct", Am J. Physiol, Mar. 1991, 260(3 Pt 2), R581-R588.

Neil et al., "Diffusion tensor imaging of normal and injured developing human brain—a technical review", NMR Biomed., Nov.-Dec. 2002, 15(7-8), 543-552.

Ogawa et al., "Oxygenations sensitive contrast in magnetic resonance image of rodent brain at high magnetic fields", Magn. Res. Med., Apr. 1990, 14(1), 68-78.

Ohta et al., "Oxygen consumption of the living human brain measured after a single inhalation of positron emitting oxygen", J. Cereb Blood Flow Metab, Mar. 1992, 12(2), 179-192.

Pekar et al., "In vivo measurement of cerebral oxygen consumption and blood flow using 17O magnetic resonance imaging", Magn. Res. Med., Oct. 1991, 21(2), 313-319.

(56) References Cited

OTHER PUBLICATIONS

Poulsen et al., "In vivo estimation of cerebral blood flow, oxygen consumption and glucose metabolism in the pig by [15O] water injection, [15O] oxygen inhalation and dual injections of [18F] fluorodeoxyglucose", J. Neurosci Methods, Dec. 1997, 77(2), 199-209.
Reddy et al., "Detection of 17O by proton T1 ρ dispersion imaging", J. Magn Reson B, Mar. 1995, 108(3), 276-279.
Recchia et al., "No metabolites accumulate in erythrocytes in proportion to carbon dioxide and bicarbonate concentration", Am J. Physiol Heart Circ Physiol, Aug. 2000, 279(2), H852-H856.
Reddy et al., "17O-decoupled 1H detection using a double-tuned coil", Magn Reson Imaging, Jun. 1996, 14(9), 1073-1078.
Rizi et al., "Proton T1ρ-dispersion imaging of rodent brain at 1.9 T", J. Magn Reson Imaging, Sep./Oct. 1998, 8(5), 1090-1096.
Stolpen et al., "17O-decoupled proton MR spectroscopy and imaging in a tissue model", J. Magn Reson, Mar. 1997, 125(I),1-7.
Tailor et al., "Proton MRI of metabolically produced H2 17O using an efficient 17O2 delivery system", Neuroimage, Jun. 2004, 22(2), 611-618.
Uttman et al., "A prolonged postinspiratory pause enhances CO2 elimination by reducing airway dead space", Clin. Physiol. Fund. Imaging, Sep. 2003, 23(5), 252-256.
Willford et al., "Decreased critical mixed venous oxygen tension and critical oxygen transport during induced hypothermia in pigs", J. Clin Monit, Jul. 1986, 2(3), 155-168.
Yokota et al., "Alveolar to arterial transmission of oxygen fluctuations due to respiration in anesthetized dogs", Pflugers Arch, Jun. 4, 1973, 340(4), 291-306.
Zhang et al., "Simplified methods for calculating cerebral metabolic rate of oxygen based on 17O magnetic resonance spectroscopic imaging measurement during a short 17O2 inhalation", J. Cereb. Blood Flow Metab., Aug. 2004, 24(8), 840-848.
Zhu et al., "Development of 17O NMR approach for fast imaging of cerebral metabolic rate of oxygen in rat brain at high field", Proc. Natl. Acad. Sci. USA, Oct. 1, 2002, 99(20), 13194-13199.
Zhu et al., "In vivo 17O NMR approaches for brain study at high field. NMR", Biomed, Apr. 2005,18(2), 83-103.

\* cited by examiner

METHOD AND APPARATUS FOR PROVIDING PULSES INHALATION OF $^{17}O_2$ FOR MAGNETIC RESONANCE IMAGING OF CEREBRAL METABOLISM

CROSS-REFERENCE TO RELATED APPLICATIONS

This application is the National Stage of International Application No. PCT/US2008/070411, filed Jul. 18, 2008, which claims the benefit of U.S. Provisional Application No. 60/951,118, filed Jul. 20, 2007, the disclosures of which are incorporated herein by reference in their entireties.

GOVERNMENT INTEREST

The present invention was supported in part by Grant Nos. R01EB004349-02 (R Reddy, PI) and RR02305 from the National Institutes of Health. The government may have certain rights in the invention.

FIELD OF THE INVENTION

The invention relates to methods and apparatuses for magnetic resonance imaging (MRI) as well as methods and apparatuses for delivery of gases by inhalation.

BACKGROUND OF THE INVENTION

Recently, several investigators have explored the use of $^{17}O$ for magnetic resonance (NMR) imaging of the cerebral metabolic rate of oxygen consumption ($CMRO_2$). For example, see Arai et al. in "*Cerebral oxygen utilization analyzed by the use of oxygen-17 and its nuclear magnetic resonance,*" Biochem. Biophys. Res. Commun. 169: 153-8, 1990; Fiat et al. in "*17O magnetic resonance imaging of the human brain,*" Neurol. Res. 26: 803-8, 2004; Hopkins et al. in "*Improved sensitivity of proton MR to oxygen-17 as a contrast agent using fast imaging: detection in brain,*" Magn. Res. Med. 7: 222-9, 1988; Ogawa et al. in "*Oxygenation-sensitive contrast in magnetic resonance image of rodent brain at high magnetic fields,*" Magn. Res. Med. 14: 68-78, 1990; Pekar et al. in "*In vivo measurement of cerebral oxygen consumption and blood flow using 17O magnetic resonance imaging,*" Magn. Res. Med. 21: 313-9, 1991; Reddy et al. in "*Detection of 17O by proton T1 rho dispersion imaging,*" J. Magn. Reson. Series B 108: 276-9, 1995; and Zhu et al. in "*In vivo 17O NMR approaches for brain study at high field. NMR,*" Biomed. 18: 83-103, 2005. Of the three naturally occurring isotopes of oxygen, only $^{17}O$, a stable non-toxic isotope, is NMR active. This nucleus has a 0.037% natural abundance, is relatively NMR insensitive, and has short relaxation times due to the quadrupolar interactions of the spin 5/2 nucleus. Gaseous $^{17}O_2$, whether dissolved in plasma or tissue, or bound to hemoglobin, is invisible to NMR detection. The $H_2^{17}O$ that is produced from $^{17}O_2$ metabolism, however, is detectable by NMR and can be measured either directly around the $^{17}O$ Larmor frequency, or with greater sensitivity by measuring the changes in $T_2$ or $T_{1\rho}$ weighted proton NMR signal caused by $^{17}O-^1H$ scalar coupling and proton chemical exchange. In contrast to other methods for imaging $CMRO_2$, therefore, $^{17}O$ approaches can detect metabolically generated labeled water without any contributions to the signal from labeled molecular oxygen.

The simplest way to deliver $^{17}O_2$ gas is by inhalation, as reported previously by Arai et al. in "*In vivo oxygen-17 nuclear magnetic resonance for the estimation of cerebral blood flow and oxygen consumption,*" Biochem. Biophys. Res. Commun. 179: 954-61, 1991; Fiat et al. in "*Determination of the rate of cerebral oxygen consumption and regional cerebral blood flow by non-invasive 17O in vivo NMR spectroscopy and magnetic resonance imaging. Part 2. Determination of CMRO2 for the rat by 17O NMR, and CMRO2, rCBF and the partition coefficient for the cat by 17O MRI,*" Neurol. Res. 15: 7-22, 1993; Fiat et al. in "*Determination of the rate of cerebral oxygen consumption and regional cerebral blood flow by non-invasive 17O in vivo NMR spectroscopy and magnetic resonance imaging: Part 1. Theory and data analysis methods,*" Neurol. Res. 14: 303-11, 1992; Tailor et al. in "*Proton MRI of metabolically produced H2 17O using an efficient 17O2 delivery system,*" Neuroimage 22: 611-8, 2004; Zhang et al. in "*Simplified methods for calculating cerebral metabolic rate of oxygen based on 17O magnetic resonance spectroscopic imaging measurement during a short 17O2 inhalation,*" J. Cereb. Blood Flow Metab. 24: 840-8, 2004; and Zhu et al. in "*Development of (17)O NMR approach for fast imaging of cerebral metabolic rate of oxygen in rat brain at high field,*" Proc. Natl. Acad. Sci. USA 99: 13194-9, 2002. For quantitative measurement of $CMRO_2$, gas mixtures enriched with $^{17}O_2$ have been administered typically as a pulse over a time period ranging from 2 minutes to 40 minutes. During this period of inhaling gas enriched in $^{17}O_2$, the $^{17}O$ is delivered to all tissues and metabolized in the mitochondria to produce $H_2^{17}O$. The change in local MRI signal is directly proportional to the amount of labeled water, and the rate of $H_2^{17}O$ production is in turn directly related to oxygen metabolism in the region of interest. The $H_2^{17}O$, however, does not just accumulate at the site of its production in the mitochondria, but also diffuses out of the local tissue to the venous circulation. Additionally, $H_2^{17}O$ produced in tissues outside of the region of interest (ROI) diffuse to their local venous circulations, and are then convectively transported to arterial blood. This $H_2^{17}O$ produced in other tissues enters the ROI in the arterial circulation, and also diffuses into tissue in the local ROI. The resulting signal is therefore a complex combination of the water production from the local $CMRO_2$ of interest, along with water migration into and out of the tissue. Interpreting the MRI signal in terms of local $CMRO_2$ specifically, therefore, can be difficult.

The present invention is directed to an alternative approach that delivers the $^{17}O_2$ in a very brief pulse, on the order of 1 minute or less. Owing to time lags for both convection and diffusion, $H_2^{17}O$ produced outside of the ROI should not have time to enter the ROI before local production of $H_2^{17}O$ has commenced. During a short enough delivery interval, therefore, the regional signal should be much simpler to interpret, primarily determined by water formed locally from the $^{17}O_2$. However, systems for mechanical ventilation are not usually designed to make a sharp step change in gas concentration, for example the pulse of $^{17}O_2$ desired in the $CMRO_2$ application. Additionally, ventilator circuits are not usually provided with a way to selectively recover parts of exhaled gas, which is enriched with very expensive $^{17}O_2$ during the pulsed administration. The present invention is directed to these needs in the art.

SUMMARY OF THE INVENTION

Provide are, inter alia, systems for mechanical ventilation that is capable of making rapid step changes in gas concentration. Methods of using such systems for the use of $^{17}O$ to image regional $CMRO_2$ is also described.

According to one aspect of the present invention, methods of delivering $^{17}O$ for the purpose of MRI imaging are provided. A pulse of $^{17}O_2$ is administered by inhalation to a patient. The pulse comprises a step increase in $^{17}O_2$ concentration. The step increase may be performed such that the patient is administered non-enriched oxygen followed by a step increase to approximately 100% $^{17}O$ enriched oxygen. The duration of the pulse may be selected to be less than the diffusion time of metabolized $H_2^{17}O$ to the region of interest to be imaged. If the pulse has a properly chosen duration, then, owing to time lags for both convection and diffusion, $H_2^{17}O$ produced outside of the ROI should not have time to enter the ROI before local production of $H_2^{17}O$ has commenced. During a short enough delivery interval, therefore, the regional MR imaging signal should be much simpler to interpret, primarily determined by water formed from the $^{17}O_2$ metabolized in the ROI. Accordingly, the duration of the pulse may be relatively short, for example, on the order of 30 to 60 seconds. MR imaging may be performed during this 30 to 60 second period in order to provide a regional NMR signal free of the effects of convection and diffusion. In addition, the need to measure the input function for $^{17}O_2$ can be eliminated by monitoring exhaled breath.

According to another aspect of the present invention, apparatuses are provided to enable a pulse of $^{17}O_2$ to be delivered by inhalation to a patient. Systems for mechanical ventilation are not usually designed to make a sharp step change in gas concentration, for example the pulse of $^{17}O_2$ used in the described method. Creating a sharp step in gas concentration at the airway imposes several restrictions on the ventilator and the breathing circuit. Tubing diameters should be small to minimize transit times and minimize diffusive slurring of concentration fronts. Sudden expansions and contractions in tubing diameter, such as might be found in typical one-way valves, are to be avoided. Flow should be unidirectional with no rebreathing of exhaled gas. An exhalation pump is preferably used to maintain the exhaled gas at a pressure and adjusting the pump speed of the exhalation pump to maintain the output pressure. Additionally, ventilator circuits are not usually provided with a way to selectively recover parts of exhaled gas. Recovery of exhaled gas is desired, for instance, when the exhaled gas is enriched with very expensive $^{17}O_2$ during the pulsed administration. A sampling bag that receives the exhaled gases after $CO_2$ scrubbing may be used for this purpose. The apparatus for mechanical ventilation provided according to an aspect of the present invention is thus capable of making rapid step changes in gas concentration, and therefore may be used with $^{17}O$ to image regional $CMRO_2$. It should be understood that the ventilation system described herein may be used with other gases and for other applications in which rapid step changes in gas concentration are desired, and to provide recovery of exhaled gas, such as functional residual capacity (FRC) determination from inert gas washout.

BRIEF DESCRIPTION OF THE DRAWINGS

FIG. 4a illustrates the MR image of a selected coronal slice from the MP-RAGE sequence, showing the relevant anatomic structures, while FIG. 4b shows signal decreases after the beginning of the $^{17}O_2$ breaths overlaid on the structural brain image.

FIG. 5a illustrates the time course of arterial $^{17}O_2$ concentrations, estimated from a model of alveolar gas dilution, while FIG. 5b illustrates the time course of a smoothed estimate of the arterial $^{17}O_2$ input function (solid line) superposed with the measured time course of the decrease in signal in the cerebral ventricle (solid circles), normalized to the signal for the entire brain.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "an pulse" is a reference to one or more of such pulses and equivalents thereof known to those skilled in the art, and so forth. When values are expressed as approximations, by use of the antecedent "about," it will be understood that the particular value forms another embodiment.

The disclosures of each patent, patent application, and publication cited or described in this document are hereby incorporated herein by reference, in their entirety.

Pulsed delivery of $^{17}O_2$ gas in large animals and humans requires a system for mechanical ventilation that has the capability to produce rapid step changes in gas concentration, to prevent rebreathing of exhaled gases that could slur step changes in gas concentrations, to provide maximal recovery of exhaled gas that is partially enriched in $^{17}O_2$, to provide minimal circuit priming volume to switch from one gas mixture to another, to provide long tubing between the ventilator mechanical apparatus outside an MRI scanner and the subject inside the scanner, to provide switching between gases with no stimulatory cues to the subject, to provide comfortable support of spontaneous breathing in awake subjects, the to provide controlled mechanical ventilation in anesthetized subjects.

Figure 1:
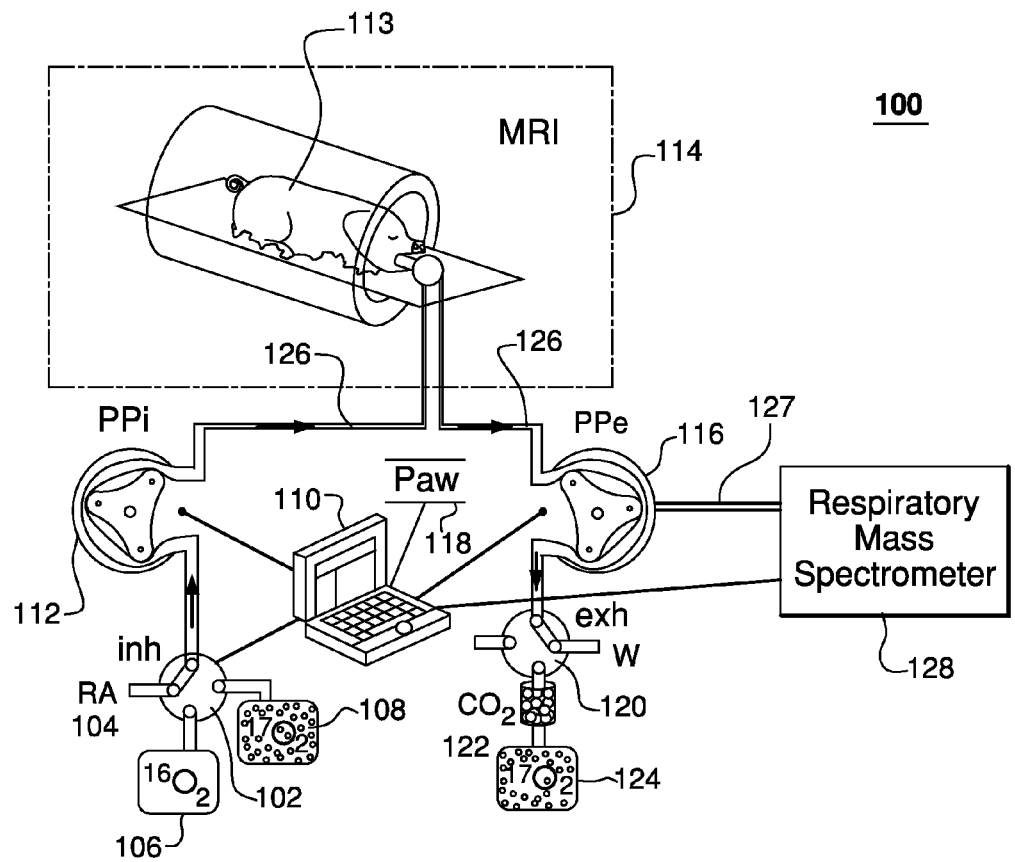
FIG. 1 is a schematic diagram of a system for mechanical ventilation in accordance with the invention for providing provides sharp step changes in $^{17}O_2$ concentrations and for recovering partially enriched exhaled $^{17}O_2$.

FIG. 1 is a schematic diagram of a system 100 for mechanical ventilation in accordance with the invention for providing provides sharp step changes in $^{17}O_2$ concentrations and for recovering partially enriched exhaled $^{17}O_2$. The inhalation stream select valve (inh) 102 selects either room air (RA) 104, 100% oxygen ($^{16}O_2$) 106, or an oxygen mixture enriched in $^{17}O_2$ ($^{17}O_2$ sampling bag 108 attached to inh), under control of computer 110. The inhalation peristaltic pump (PPi) 112 pressurizes the selected gas and delivers it to the subject 113 in the MRI scanner 114, also under control of computer 110. Exhalation is actively assisted via the exhalation peristaltic pump (PPe) 116, according to the airway pressure transducer (Paw) 118. Exhaled gas is directed by the exhalation stream select valve (exh) 120 to either waste (W) or through a carbon dioxide absorbent ($CO_2$) 122 to a recovered $^{17}O_2$ sampling bag 124 attached to exh 120 as indicated in FIG. 1.

During operation of the system of FIG. 1, gases are pumped to and from the subject 113 by two large peristaltic pumps 112 and 116 (Cole Parmer, Chicago Ill.; Masterflex I/P digital drive with dual standard pump heads and silicone I/P 73 tubing), with pump 112 for assisting or controlling inhalation, and pump 116 for assisting or controlling exhalation. The pumps 112, 116 outside of the MRI scanner 114 are connected to the subject 113 inside the MRI scanner 114 by, for example, 25 feet of 0.25 inch ID Tygon® tubing 126 (Cole Parmer L/S 17). Pressure at the subject's airway is transmitted by 0.125 inch ID nylon tubing to pressure transducer 118 (Freescale Semiconductor, Chandler, Ariz., MPX2010DP) with signal amplification by a custom op-amp circuit (not shown). Information on airway pressure is transmitted by pressure transducer 118 via a multifunction DAQ device (National Instruments, Austin Tex., USB-6008) to computer 110, which uses feedback control to adjust the pump speeds for both pumps during assisted spontaneous ventilation and for the exhalation pump 116 during volume-controlled mechanical ventilation Inhaled gases are chosen via computer controlled stream select valve 102 (VICI Valco Instruments, Houston, Tex., Model C45) to select air 104, regular 100% $O_2$ 106, or oxygen with enriched $^{17}O_2$ 108. The oxygen gases are sealed in Tedlar® gas sampling bags (Cole Parmer). Exhaled air can be directed, via stream select valve 120 to either waste or to recovery of the partially enriched $^{17}O_2$ gas sampling bag 124 during and after an administered pulse. Carbon dioxide absorbent 122 removes $CO_2$ from the recovered, exhaled gas.

The long tubing connections between the mechanical components and the subject 113 required a significant departure from prior approaches to mechanical ventilation. Although a wide variety of ventilator modes are available from conventional ventilators, exhalation is almost universally passive, i.e. the exhalation pressure at the ventilator is set to a prescribed value and the lungs exhale passively against that exhalation pressure. Ventilator exhalation tubing is usually sized in a large enough diameter to make expiratory flow resistance negligible, thus keeping the pressure at the airway equivalent to the set exhalation pressure in the ventilator. For the system of FIG. 1, however, large bore exhalation tubing would greatly increase the circuit priming volume, and would also tend to slur any sharp concentration fronts in the exhalation limb, making clean recovery of partially enriched $^{17}O_2$ more difficult. Passive exhalation, therefore, leads to design requirements for the exhalation tubing that are fundamentally at odds with the requirement for efficient use and recovery of the expensive $^{17}O_2$ gas. The system depicted in FIG. 1 approaches these problems by actively assisting exhalation as well as inhalation. Pressure at the airway is monitored and fed back to the control system, which then adjusts the exhalation pump speed. The target exhalation pressure at the airway can then be specified at any given level, and for the subject it appears they are exhaling passively at that pressure, even though the pressure required at the end of the exhalation tubing varies markedly according to expiratory flow rate.

At the inspiratory side, mechanical ventilators typically have a gas bellows that slurs rapid step changes in gas concentration (see Huygen et al. in "Design and validation of an indicator gas injector for multiple gas washout tests in mechanically ventilated patients," Crit. Care Med. 18: 754-9, 1990), and again increases the circuit priming volume. Accordingly, an additional roller pump (not shown) was used to eliminate the reservoir volume and to avoid any large changes in tubing diameter, helping to preserve step changes in gas concentration. The use of inspiratory pump 112 also does not require pressurized gas sources, an advantage in developmental experimental work where a single mishap with a gas tank regulator could result in a large waste of precious $^{17}O_2$ gas.

The system for mechanical ventilation as illustrated in FIG. 1 has been tested in two settings: (1) testing in a human volunteer in spontaneous ventilation mode, with use of helium as a surrogate for $^{17}O_2$, and with monitoring of gas concentrations at the airway with a respiratory mass spectrometer; and (2) testing in an anesthetized pig with controlled ventilation, administration of $^{17}O_2$, and MRI imaging of the brain.

Mass Spectrometer Assessment of Ventilation System Performance:

A micropore membrane inlet probe with a silicone membrane was used as the inlet system for a quadrupole mass spectrometer 128 (Stanford Research Systems, Sunnyvale, Calif., RGA200). Gas was drawn at 5 ml/min over the MMIMS (micropore membrane inlet mass spectrometry) probe 127 by a peristaltic pump (not shown), through 60 cm of 0.020 inch ID tubing between the sampling tip and the pore of the MMIMS probe 127. The time response of the inlet system and mass spectrometer 128 were determined by placing the sample port in a stream of flowing gas, directly downstream of a switching valve (Valco Instruments Model C45), and switching the gas source from 0% to 100% helium. One could also measure concentrations at the patient's mouth with a respiratory mass spectrometer, but this would add significant cost and complexity to the system.

A human volunteer breathed through the circuit in assisted spontaneous ventilation mode, where both inspiratory and expiratory pump flows were controlled by the pressures generated at the airway by the subject. Airway gas concentration of helium was monitored throughout the experiment with the respiratory mass spectrometer 128. After switching to 100% $O_2$ and denitrogenation, the inhalation valve 102 was switched to a source gas of 100% helium and the change in gas concentration at the airway was recorded by the mass spectrometer 128. After two inhaled breaths of helium, the source valve 102 was switched back to 100% oxygen. Exhaled gas was directed, by the exhalation valve 120, to the "recovered $^{17}O_2$" gas sampling bag 124 for these two breaths of helium and for the following three breaths. Helium concentration in the "recovered $^{17}O_2$" bag 124 was then measured with the respiratory mass spectrometer 128.

$^{17}O_2$ Administration and Imaging:

To further test the apparatus 100, a 70 Kg Yorkshire pig was anesthetized with intramuscular doses of ketamine (25 mg/Kg) and xylazine (2.5 mg/Kg) and orally intubated. General anesthesia was maintained throughout the experiment with intravenous doses of ketamine (1-2 mg/Kg/hr) and diazepam (0.5-1 mg/Kg/hr). Once placed in the MRI scanner 114 in the prone position, the endotracheal tube was connected to the circuit and mechanical ventilation commenced in volume control mode with a tidal volume of 16.2 ml/Kg, a respiratory rate of 6 breaths/min, I:E ratio of 1:1 and zero end-expiratory pressure. After collecting baseline images on room air, the source valve was switched to 100% $O_2$. After 5 minutes to allow for denitrogenation, further baseline images were obtained while breathing 100% oxygen. The source valve 102 was switched to $^{17}O_2$ for 2 breaths (40% enrichment; Isotec, Miamisburg, Ohio), and then back to 100% $O_2$, during continuous acquisition of images at a frequency of 1 image per 23 seconds. Exhaled gas was recovered in the exhalation bag 124 for the 2 breaths of $^{17}O_2$ and the following 3 breaths.

The time course of the arterial concentration of $^{17}O_2$ during this pulsed delivery of $^{17}O_2$ was estimated with a simple model of the kinetics of alveolar gas concentration changes. If it is assumed that tidal gas mixes completely on entering the alveolus, the changes in average alveolar concentration will be determined by the inspiratory flow rate and the end-expiratory lung volume. Changes in alveolar gas concentrations due to blood uptake, both in inspiration and expiration, were neglected. The alveolar gas concentration was therefore modeled as increasing during the two $^{17}O_2$ inhalations in two steps, with steady plateaus during exhalation. After the $^{17}O_2$ breaths, the decrease in average alveolar concentration was modeled as a similar series of decays. Finally, the assumption was made that arterial gas concentrations follow the same time course as the alveolar gas changes, i.e. it was assumed that arterial $^{17}O_2$ concentrations were in equilibrium with average alveolar $^{17}O_2$ concentrations.

Imaging Apparatus and Parameters:

The MRI scanner 114 in an exemplary embodiment has a magnetic field strength of 1.5 Tesla and is equipped with a standard receive-only human birdcage-design head coil. In the experimental setup, the full-body transmitter was used for transmission. A standard T1-weighted localizer sequence was run to find a suitable coronal image of the middle portion of the pig brain that included cortex, brainstem, and ventricle. A T1-weighted MP-RAGE sequence was performed to obtain an anatomical image of the desired slice. Comfortable breathing and stable imaging were confirmed by five minutes of room air breathing during serial $T_{1\rho}$ weighted images. The $T_{1\rho}$ sequence used was based on turbo spin echo following a phase-alternating spin-lock cluster. Sequence parameters were as follows: TR/TE 2000/12 ms, field of view 20 $cm^2$, 256×128 matrix, 5 mm slice thickness, echo train length 13, averages 1, bandwidth 130 Hz/Px, turbo spin lock pulse amplitude 200 Hz, spin lock pulse length 120 ms, scan time 23 sec/image. Images were acquired continuously from the single 5 mm thick coronal slice, throughout the $^{16}O_2$ breathing and the $^{17}O_2$ pulse.

Figure 2:
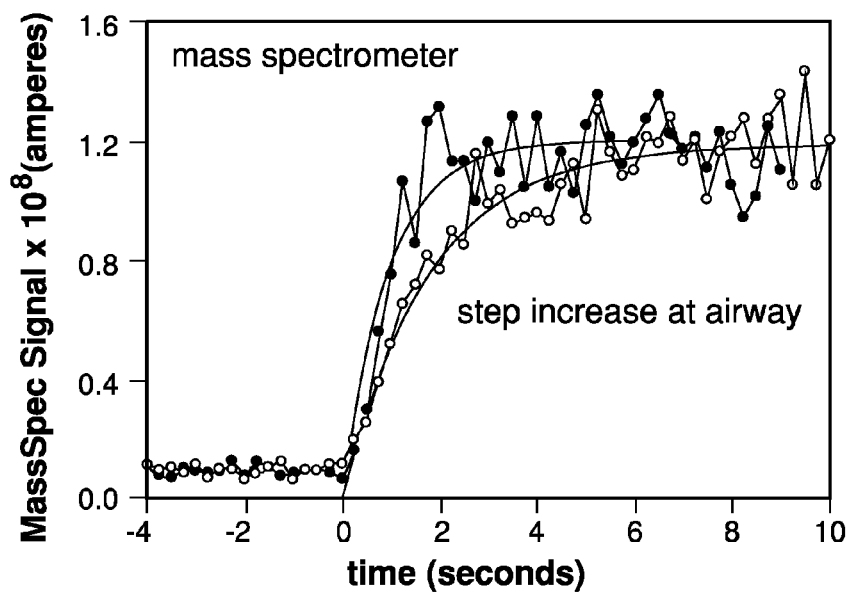
FIG. 2 illustrates the intrinsic mass spectrometer time response for a 0-100% step in helium partial pressure (solid circle s); and measured change helium partial pressure at the airway after a switch from 100% oxygen to 100% helium in the complete breathing circuit (open circles).

Mass Spectrometer Assessment of Ventilation System Performance:

The inhalation and exhalation pump flow changes in response to changes in airway pressure were adequate to provide subjectively comfortable spontaneous breathing in the normal human subject. FIG. 2 illustrates the intrinsic mass spectrometer time response for a 0-100% step in helium partial pressure (solid circles); and measured change helium partial pressure at the airway after a switch from 100% oxygen to 100% helium in the complete breathing circuit (open circles). Both step responses are fit with a monoexponential rise for measuring the 0-90% response time. As shown in FIG. 2, the 0-90% response time of the respiratory mass spectrometer 128 was 2.2 seconds. The step change in gas concentration at the airway provided by the ventilator circuit was fast enough to approach the temporal resolution of the mass spectrometer 128, with a measured 0-90% response time of 4.0 seconds. After correction for the mass spectrometer time response by deconvolution, the estimated 0-90% response time at the airway was 2.4 seconds.

Figure 3:
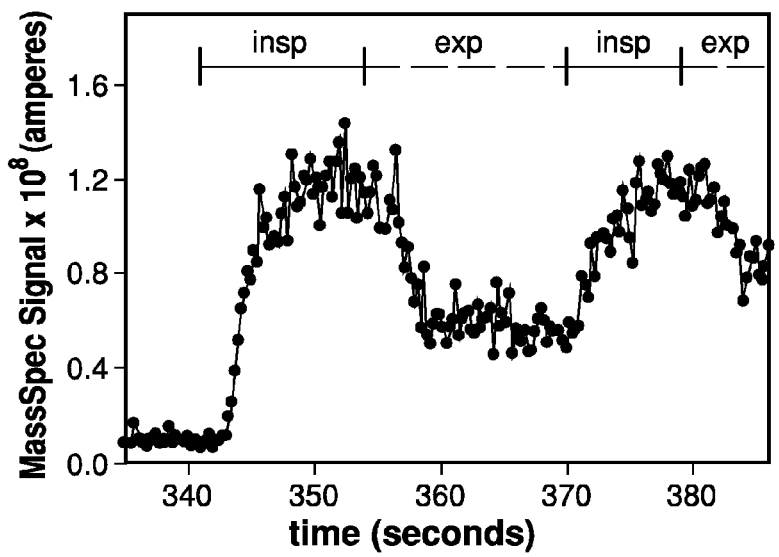
FIG. 3 illustrates the helium concentration at the airway for two breaths of 100% helium after equilibration with 100% oxygen.

The time course of helium concentration changes at the airway during two breaths of helium are shown in FIG. 3, with labeling of the phases of the respiratory cycle. The measured end tidal helium concentration after a single deep breath was 41%. After further practice by the subject breathing as deeply as possible with the ventilator system, the end-tidal helium after a single deep breath was 48%. This compares favorably with an estimate based on lung volumes determined from standard nomograms. For a normal human subject 1.85 meters tall, exhaling deeply and inhaling deeply, residual volume is predicted to be 2.41 liters; tidal volume can be estimated by the predicted forced vital capacity (FVC) at 4.94 liters, and anatomic deadspace volume is predicted to be 156 ml, giving an estimated end tidal helium concentration of 65% after a single deep breath of helium. The slightly reduced measured end tidal concentration, compared to predicted norms, is consistent with slight residual circuit breathing resistance compared to the apparatus typically used to measure FVC.

The measured concentration of helium in the "recovered $^{17}O_2$" gas sampling bag 124 was 47%. The recovered gas concentration can also be reasonably predicted by a simple model of gas exhalation. For a tidal volume, end-expiratory volume, and deadspace volume predicted by nomograms as above, and treating the exhaled gas profile as a deadspace with the inhaled gas concentration followed by a constant alveolar plateau at the end-tidal gas concentration, the predicted helium concentration in the recovered bag was 40%.

Figure 4:
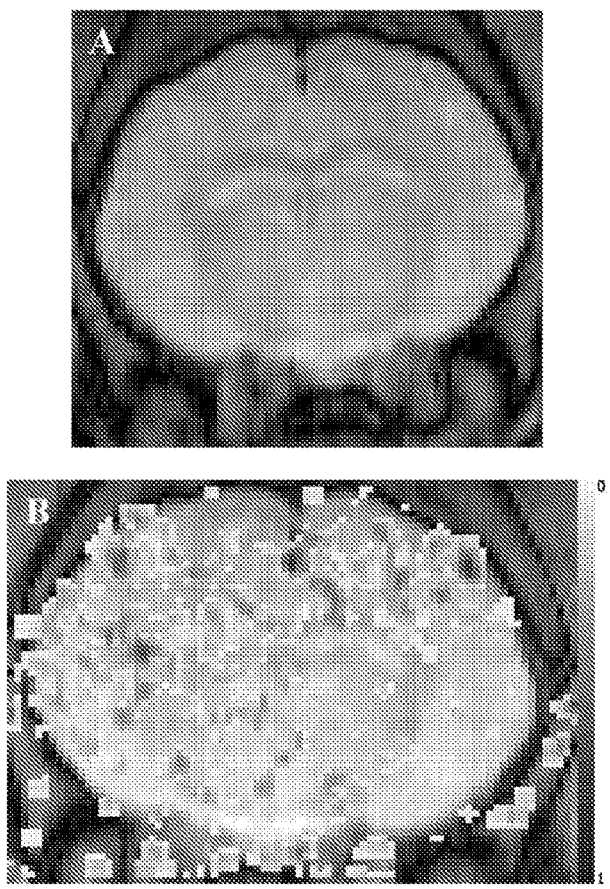

$^{17}O_2$ Administration and Imaging:

The MR image of the selected coronal slice from the MP-RAGE sequence, showing the relevant anatomic structures, is presented in FIG. 4a, while FIG. 4b shows signal decreases after the beginning of the $^{17}O_2$ breaths overlaid on the structural brain image. Overlay of the signal decreases, ranging from 0% decrease to 1% decrease, an average of 40-50 seconds after the start of the $^{17}O_2$ breaths, as determined by indirect $T_{1\rho}$ imaging with a spin-lock sequence. Thus, the duration of the pulse may be relatively short, for example, on the order of 30 to 60 seconds. For the $H_2^{17}O$ images, 3 sequential images (23 seconds per image) after the beginning of the $^{17}O_2$ pulse are averaged and compared to the baseline breathing $^{16}O_2$ immediately before the $^{17}O_2$ pulse. Metabolic production of $H_2^{17}O$ is expected to decrease the signal, compared to baseline, as suggested in several brain regions, notably regions of parietal cortex bilaterally. It should be noted, however, that statistical analysis of sequential time series data in any given parenchymal regions of interest did not show a statistically significant signal decrease, owing to the low signal to noise ratio with the specified imaging parameters.

Figure 5:
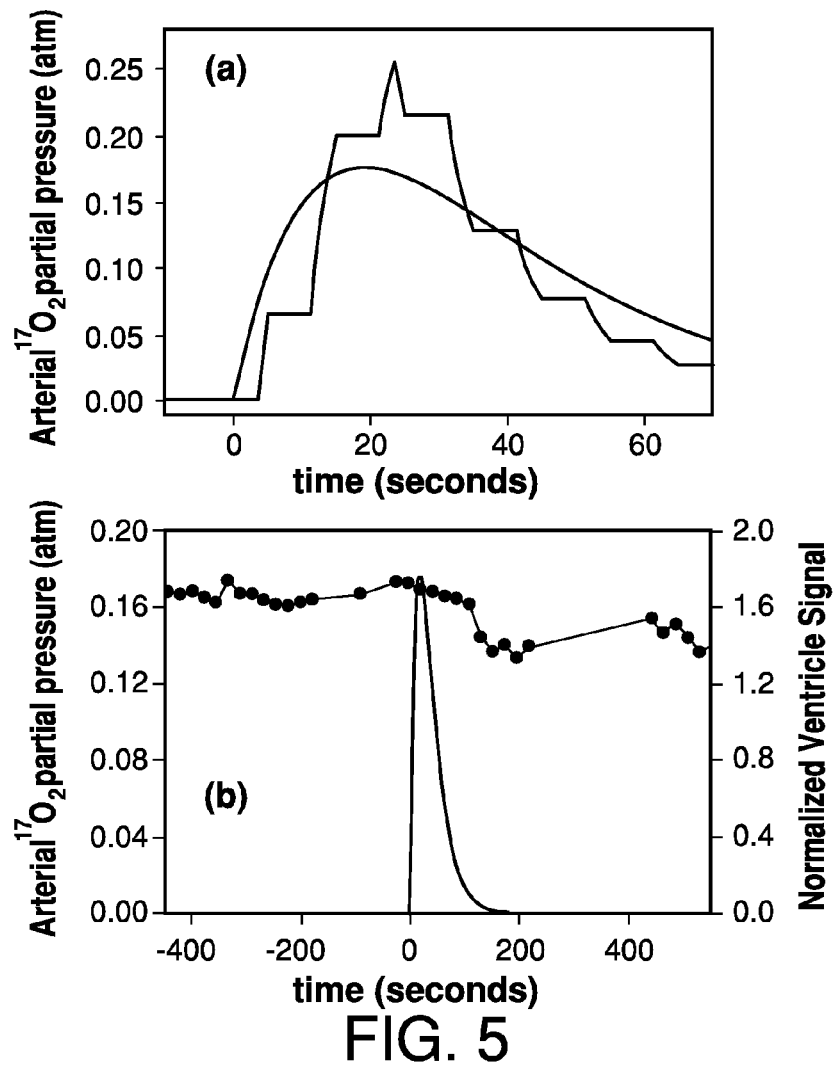

The time course of arterial $^{17}O_2$ concentrations, estimated from a model of alveolar gas dilution (appendix), is shown in FIG. 5a. Parameters for the gas dilution model include tidal volume and end-expiratory volume. Inspiratory tidal volume is measured from the calibrated output of the inhalation pump 102. As shown in FIG. 5a, time courses of the calculated arterial $^{17}O_2$ concentration changes (steps and plateaus) along with a smoothed fit to the data determined by non-linear regression. The fitted function, $y=K[k_a/(k_a-k_e)][\exp(-k_e t)-\exp(-k_a t)]$, is a standard single compartment pharmacokinetic model with exponential washin and washout, where $k_a$ and $k_e$ are absorption and elimination constants. Best fit parameters are K=0.481 atm, $k_a$=0.0523 sec$^{-1}$, and $k_e$=0.0524 sec$^{-1}$. At an end exhalation pressure of zero, the relevant end-expiratory volume is the functional residual capacity (FRC), which was estimated as 17.3 ml/Kg. FIG. 5a shows the results from the alveolar dilution model, with the $^{17}O_2$ changes occurring as a series of step increases and decreases during inspiration, followed by plateaus during exhalation. The smoothed fit in FIG. 5a facilitates the visualization of the $^{17}O_2$ kinetics in the longer time scale of FIG. 5b, where the $^{17}O_2$ kinetics and normalized ventricular $H_2^{17}O$ kinetics are superposed. As shown in FIG. 5b, the time course of a smoothed estimate of the arterial $^{17}O_2$ input function (solid line) is superposed with the measured time course of the decrease in signal in the cerebral ventricle (solid circles), normalized to the signal for the entire brain. The steady state signal in the ventricle is reduced compared to baseline as a consequence of the larger decrease in MR signal for $H_2^{17}O$ in CSF compared to $H_2^{17}O$ in tissue. The decrease in scaled signal in the cerebral ventricle is delayed for about 110 seconds after the initial inhalation of $^{17}O_2$. The delay in the ventricular signal decrease, after the initial $^{17}O_2$ breaths, of about 110 seconds is readily apparent.

$^{17}O$ offers some significant advantages for imaging of $CMRO_2$ (and metabolic rate of oxygen utilization in other tissues), mainly owing to the fact that the gaseous $^{17}O_2$ does not produce an MRI signal but the water produced by metabolism does produce an MRI signal. In past studies, however, interpretation of the MRI signal in terms of regional $CMRO_2$ has been complicated by the entrance, into the region of interest, of water produced by oxygen metabolism in other tissues. The pulsed approach to $^{17}O_2$ delivery in accordance with the invention takes advantage of kinetic differences in the behavior of $^{17}O_2$ gas versus $H_2^{17}O$ water. If it were physically possible to produce a step increase in arterial $^{17}O_2$ and keep this $^{17}O_2$ level constant for several minutes, early in the pulse there should be a delay in metabolic $H_2^{17}O$ production as the gas diffuses from capillary blood to the mitochondria. This diffusive delay is characterized by the time constant $\delta^2/D$, the average diffusing distance squared divided by the diffusivity of oxygen in tissue. For an average capillary spacing in brain of 50 microns, each capillary can be estimated to supply a cylinder of radius 25 microns. The spatially averaged diffusing distance, assuming uniform distribution of mitochondria around the capillary, is then estimated at 17 microns. For a simple one-dimensional diffusion model into a finite slab, solution to the transient diffusion equation with an oxygen diffusivity in tissue of $2.4 \times 10^{-5}$ cm$^2$/second estimates that the average 0-90% rise time in mitochondrial concentration after a step change in arterial concentration would be approximately 130 msec. This diffusional delay in mitochondrial $^{17}O_2$ utilization can therefore be neglected for all but the shortest arterial pulses. After this negligible diffusion time lag, the MRI signal in the ROI should increase as $H_2^{17}O$ is produced from oxygen metabolism. For a brief interval after this, the regional signal should be determined primarily by the regional $CMRO_2$, and secondarily by the diffusion of $H_2^{17}O$ out of the ROI. The arterial input for recirculated $H_2^{17}O$, however, should have an additional time delay, in part due to diffusion time lag and in part due to a convection time lag.

First the water produced in mitochondria of other tissues must diffuse to the capillaries and venules. This time lag is again proportional to $\delta^2/D$, but now with the diffusivity of water in tissue. Estimation of this diffusion lag for water is not as straightforward as the diffusion lag for oxygen, because the appropriate water diffusivity in tissue is not known with any precision. If the relevant diffusivity is the average isotropic diffusivity of water in cortex, reported to be around $0.7 \times 10^{-5}$ cm$^2$/sec (Neil, J., J. Miller, P. Mukherjee, and P. S. Huppi. *Diffusion tensor imaging of normal and injured developing human brain—a technical review.* NMR Biomed. 15: 543-52, 2002), the 0-90% response time for a change in capillary concentration after a step change at the mitochondria is estimated as 430 milliseconds, again negligible for all but the briefest pulses. Diffusion of water through lipid bilayers, however, is known to be restricted, and the newly generated $H_2^{17}O$ may be substantially delayed in traversing first the mitochondrial, then the plasma, and finally the capillary endothelial membranes to reach the venous circulation Inner mitochondrial membrane of hepatocytes has been reported to contain aquaporin 8 (AQP8) channels that should substantially increase the water permeability, but the magnitude of this effect in intact mitochondria, and whether AQP8 is present in mitochondria of other cells, is not currently known. For brain, it has been recently reported by Zhu et al. that the washout of $H_2^{17}O$ generated metabolically inside the mitochondria is substantially slower than the washout of $H_2^{17}O$ delivered into tissue by an arterial bolus, suggesting restricted diffusion through the mitochondrial membrane. An additional factor that would delay the appearance of water in the venous circulation is the increased average diffusing distance in most non-cerebral tissues, which generally have a lower metabolic activity and lower capillary density than brain, with the exception of heart and maximally exercising skeletal muscle.

After this diffusional delay, there is an additional delay for convective transport from the venous drainage of tissue, to the right heart, through the lungs and left heart, and to the arterial circulation in the ROI. For a normal sized adult human, a typical venous to arterial transit time is in the range of 10-18 seconds with a slightly longer time required for transit from systemic capillaries to cerebral arterioles. One would expect a similar convective time lag in a 70 Kg pig. The time delay for the appearance of $H_2^{17}O$ in the arterial circulation is therefore predicted to be on the order of at least 10-15 seconds, with longer delays if water diffusion in tissue is restricted. More restricted diffusion of water in tissue translates into longer delays in the $H_2^{17}O$ arterial input function, as well as delayed egress of locally produced $H_2^{17}O$ in the brain, which in turn would increase the effectiveness of pulsing the $^{17}O_2$ delivery.

The definitive data for determining the delay in the $H_2^{17}O$ arterial input function in this large animal subject would be a direct measurement of $H_2^{17}O$ in a large artery in the field of view, but this is currently beyond the spatial resolution and signal to noise ratio limits of the inventors' imaging apparatus. The normalized signal for the cerebral ventricle (FIG. 5b), however, does suggest a substantial diffusion delay. The ventricle is a good ROI for detecting small signals in a large noise background for several reasons. First, for equal concentrations of $H_2^{17}O$ in CSF and in tissue, the MR signal decrease is expected to be different in CSF versus tissue. Therefore after a pulse of $^{17}O_2$, once a new steady state is achieved with equal $H_2^{17}O$ concentrations throughout the body, the scaled steady state signal for CSF will be changed compared to baseline even when normalized to the whole brain signal. Normalizing the signal from the ventricle to the signal from the entire brain improves the SNR by negating global artifacts such as such as scanner start-up transients and artifacts from small movements during the sequential images. Second, the ventricle is a relatively large and homogenous structure, with easily recognized borders, and with many voxels for signal averaging.

$H_2^{17}O$ can enter the ventricle by three routes—direct secretion by choroid plexus, diffusion from mitochondria adjacent to the ventricle, and diffusion from choroid capillaries once the systemic arterial and capillary concentrations of $H_2^{17}O$ have increased. Secretion by choroid plexus is a slow process and can be neglected on a time scale of several minutes. Diffusing distances from the $H_2^{17}O$ produced in adjacent mitochondria, however, are small, as are the diffusion distances between choroid plexus capillaries and CSF. The measured delay in ventricular signal decrease of approximately 110 seconds (FIG. 5), therefore, suggests that water diffusion in tissue is not free but substantially restricted, and also suggests that the arterial input function of $H_2^{17}O$ is delayed beyond the 10-15 seconds of convective delay.

Although delivering $^{17}O_2$ as a brief pulse can simplify the interpretation of the MRI signal, it also presents some substantial challenges. For example, the pulse creates a sharp step change in gas concentration in the ventilator circuit and complicates estimating the time course of arterial $^{17}O_2$ concentrations, acquiring MRI images with adequate time resolution and SNR, and quantitatively determining $CMRO_2$ from the MRI signal. These issues are addressed below.

Creating a Step Change in Gas Concentration

Meeting the requirements for mechanical ventilation in accordance with the techniques of the invention requires a substantial departure from prior ventilators. Creating a sharp step in gas concentration at the airway imposes several restrictions on the ventilator and the breathing circuit. Tubing diameters should be small to minimize transit times and minimize diffusive slurring of concentration fronts. Sudden expansions and contractions in tubing diameter, such as might be found in typical one-way valves, are to be avoided. Flow should be unidirectional with no rebreathing of exhaled gas. The ventilator system presented here is clearly capable of a rapid step change in gas concentration, as shown in FIG. 2. Of note, there are other applications that could benefit from the ability to make a sharp step change in gas concentration, such as FRC determination from inert gas washout.

Estimation of the Arterial $^{17}O_2$ Kinetics

After a step change in gas concentration at the airway, kinetics of gas dilution in the lung become the major determinant of the time course of both alveolar and arterial changes in $^{17}O_2$ concentrations. The arterial $^{17}O_2$ kinetics may be estimated with a simple model of this gas dilution that includes the known inspiratory flow pattern from the inhalation pump. This model estimates the time course of arterial $^{17}O_2$ concentrations as a function of time by determining from nomograms for lung volumes the measured inspiratory flow pattern, and the known inspired $^{17}O_2$ concentration, using established principles of alveolar gas mixing. In the general case, the approximation can be obtained easily with the evaluation of 2 integrals. In the particular case examined here, with fixed inspiratory concentration and constant inspiratory flow, the integrals reduce to a simple algebraic equation for alveolar $^{17}O_2$ concentration that can be applied recursively to estimate the arterial $^{17}O_2$ input function over several breaths.

At end-exhalation, the lung is filled with a residual alveolar volume as well as deadspace volume in the airways. It is assumed that these two gas volumes are well mixed and at the same gas concentration at the end of exhalation. During the first part of inspiration, the deadspace gas re-enters the alveolus with no change in alveolar gas concentration. It is assumed as an approximation that the inspired gas/deadspace gas interface is transmitted to the alveolus as a sharp step change in concentration. At the moment this concentration front is entering the alveolus, the alveolar gas volume is the end-exhalation volume plus deadspace volume, at the end-exhalation gas concentration. From this point forward, the total amount of $^{17}O_2$ in the alveolar space, Y(t), at time t is given by:

$$Y(t) = \left[\int_0^t \left(\frac{d}{d\tau}V\right) \cdot P_i(\tau)d\tau\right] + (V_d + V_{ee}) \cdot P_{ET}$$

where $P_{ET}$ is the end tidal $^{17}O_2$ partial pressure at the last exhalation, $V_{ee}$ is the end-expiratory volume, $V_d$ is the deadspace volume, dV/dt is the flow rate as a function of time, and $P_i(t)$ is the inspired $^{17}O_2$ partial pressure as a function of time. The total alveolar gas volume, X(t), as a function of time is given by:

$$X(t) = \left[\int_0^t \left(\frac{d}{d\tau}V\right)d\tau\right] + (V_d + V_{ee})$$

The alveolar gas partial pressure versus time during inhalation is then simply Y(t)/X(t). For the large tidal volumes used in accordance with the invention, the delivery of $^{17}O_2$ in each breath far exceeds the gas volume taken up by blood, and to a first order blood uptake can be neglected.

Airways deadspace volume in the pig was estimated from a prior report by Uttman et al. in "*A prolonged postinspiratory pause enhances CO2 elimination by reducing airway dead space*," Clin. Physiol. Funct. Imaging 23: 252-6, 2003, as was the end-expiratory volume at zero end-expiratory pressure by Ludwigs et al. in "*A comparison of pressure- and volume-controlled ventilation at different inspiratory to expiratory ratios*," Acta. Anaesthesiol. Scand. 41: 71-7, 1997. The ventilator system presents a fixed $^{17}O_2$ partial pressure throughout inspiration. In accordance with the methods described herein, the target inspiratory flow was set to a constant value throughout inhalation, with the constant inspiratory flow determined by the software to achieve a specified tidal volume. The peristaltic pump, however, takes about 1 second to accelerate from a speed of zero to the target speed. As a result, for the settings in this study, the first 1.25 seconds of inspiration delivered the deadspace volume, and at all times after that the inspiratory flow rate was constant at 252 ml/second. Taking 1.25 seconds into inspiration as t=0, the alveolar gas concentration changes in inspiration are therefore given simply by:

$$P_{alv}(t) = \frac{(P_I \cdot 252 \cdot t) + (V_d + V_{ee}) \cdot P_{ET}}{252 \cdot t + V_d + V_{ee}}$$

where $P_I$ is the constant inspired partial pressure in the current inspiration and $P_{ET}$ is the end tidal partial pressure in the last exhalation. To first order, it is assumed that the alveolar concentration does not change during exhalation. The algebraic formula was therefore applied recursively to estimate the alveolar concentration of $^{17}O_2$ starting with two breaths at the inspired partial pressure of 0.40 atm, and then following washout for several breaths. Similar principles were applied to the first inhalation (after switching the source gas from regular $^{16}O_2$ to the enriched 40% $^{17}O_2$) and the third inhalation (after switching the source gas back to regular $^{16}O_2$), with accounting for the deadspace volume of the inhalation limb of the circuit, and also the small amount of slurring of the new gas/old gas concentration step after transiting the inhalation limb (FIG. 2). As an approximation, the new gas/old gas front was treated as a sharp step at the midpoint of the slurred concentration profile, which was identified by the equal area method. Finally, it was assumed that arterial concentrations were equal to alveolar concentrations at all times.

This model aims to incorporate the major features of this alveolar gas dilution, and does not include several other features that have been presented in more elaborate models of alveolar gas kinetics. Some factors that could influence arterial $^{17}O_2$ changes include: (1) heterogeneity of alveolar gas concentrations; (2) uptake and exchange of $^{17}O_2$ with pulmonary blood; (3) changes in alveolar volumes and $CO_2$ concentrations during exhalation; (4) the slurred concentration front between tidal volume gas and alveolar gas; and (5) factors such as mixing in the left ventricle that could slow arterial kinetics compared to alveolar kinetics (See Yokota et al. in "*Alveolar to arterial transmission of oxygen fluctuations due to respiration in anesthetized dogs,*" *Pflugers Arch.* 340: 291-306, 1973). The purpose here, however, is to present a reasonable approximation of the arterial $^{17}O_2$ time course that demonstrates the principles and potential of pulsed $^{17}O_2$ delivery. Gains to be had from adding more detail to the model would probably be small, particularly in the absence of experimental data to test the modeling. No technology currently is capable of measuring alveolar $^{17}O_2$ concentrations with high time resolution. Similarly, no method has been reported for high temporal resolution measurements of $^{17}O_2$ in arterial blood, although the MMIMS technology does offer some potential in this regard.

Technical Challenges of the Indirect Imaging Method

In order to develop signal contrast based on small differences in relaxation, long times to echo or long spin locking times are required. However, signal from the image decays during this relaxation, resulting in images with inherently less signal-to-noise than conventional anatomic MR images. For example, the signal to noise in this series of images was calculated to be about 15:1. To improve the SNR, and temporal and spatial resolution, other sequences to apply the $T_{1\rho}$ method to this application are currently being explored. Candidate sequences include spin lock pre-encoding with gradient recalled echoes (GRE), echo planar imaging (EPI), spin-echo echo planar imaging (SE-EPI), and balanced steady state free precession readouts (bSSFP). Long spin locking times also challenge the scanner hardware requirements because they magnify coil inhomogeneity ($B_1$) artifacts that are much less pronounced with more homogenous small animal scanners and coils.

Quantitatively Determining $CMRO_2$ from the MRI Signal

The ultimate goal of the pulsed delivery of $^{17}O_2$ is to provide high resolution imaging of local oxygen metabolism. Quantitative determination of $CMRO_2$ requires a mathematical model relating the time course of changes in local concentration of $H_2^{17}O$ to oxygen metabolism. Zhu et al. have presented a comprehensive model of the relationship between local concentration of $H_2^{17}O$ and $CMRO_2$, based on the mass balance principles first developed by Kety and Schmidt in "*The nitrous oxide method for the quantitative determination of cerebral blood flow in man: theory, procedure and normal values,*" *J. Clin. Invest.* 27: 476-483, 1948. In their model, the time rate of change of tissue $H_2^{17}O$ concentration $C_b(t)$ is directly related to $CMRO_2$, plus terms that represent $H_2^{17}O$ entering the ROI from recirculation, and $H_2^{17}O$ leaving the ROI in venous blood. During a brief enough pulse, the arterial input function is identically zero, greatly simplifying the model and its experimental application by deleting a major term. As a first order approximation, venous losses can also be neglected on the grounds that water diffusion from the mitochondria tends to be restricted. As anticipated, the resulting relationship between $H_2^{17}O$ concentration and $CMRO_2$, for a brief pulse, is quite simple:

$$CMRO_2 = k_1(dC_b(t)/dt)/C_a(t)$$

where $C_a(t)$ and $C_b(t)$ are the $^{17}O_2$ concentrations in arterial blood as a function of time at times a and b, and $k_1$ is a conversion constant. Application of this simple model quantitatively requires adequate acquisition times to trace out the regional time course of $H_2^{17}O$ as the arterial $^{17}O_2$ function is rapidly changing. For qualitative comparisons, however, the pulse approach does show potential for distinguishing areas of high versus low metabolism, even with fairly slow image acquisition (FIG. 4), provided that the signal-to-noise ratio can be improved.

EXAMPLE

Demonstration of Feasibility of Measuring $CMRO_2$

Experiments were designed to measure the kinetics of metabolically produced $H_2^{17}O$ after conversion from $^{17}O_2$ in the swine brain and determine the time period during which there is no significant recirculation of $H_2^{17}O$ from other regions. The experiments were also conducted with the aim of demonstrating the feasibility of measuring the cerebral metabolic rate of oxygen consumption ($CMRO_2$) in swine with circulatory and respiratory systems similar to humans.

The methodology involved delivery of only about one tidal volume of $^{17}O_2$ by a custom, minimal-loss, precision-delivery breathing circuit. A model for gas arterial input function (AIF) is therefore presented for large animals. The AIF of recirculating metabolic water was measured by arterial blood sampling and $^{17}O$ spectroscopy. The $CMRO_2$ was estimated with rapid $T_{1\rho}$-weighted proton MRI on a 1.5 T clinical scanner as well as with $^{17}O$ spectroscopy at 3 T.

It has been found that minimal metabolic water "wash-in" occurs before 60 seconds after delivery. Hemispheric $CMRO_2$ is estimated during that time at 1.33±0.26 μg/g/min, consistent with existing literature values. Therefore, it has been demonstrated that there is ample time before significant recirculation of metabolic $H_2^{17}O$ to brain and use this information to compute the $CMRO_2$ in swine. The methodology developed herein can be easily adapted to human studies on standard clinical scanners.

Breathing Circuit Design.

The precision delivery circuit used was developed for gas experiments to provide step changes in concentration of gas at the mouth with precise timing and minimal gas loss. Its design appears schematically in FIG. 1. When used with large animals as in the experiments described here, respiratory rate is set to 6 breaths/min and a tidal volume of 18 times the weight in kg. In these experiments, 1.2 times the tidal volume of enriched $^{17}O_2$ was diluted with nitrogen to a final concentration of 20% enriched $^{17}O_2$ and 80% $N_2$ and delivered over 6 breaths. Delivery begins at time 0 in all plots.

Briefly, the Precision Delivery Circuit connects from outside the magnet room through three sets of tubing to the endotracheal tube of a large animal subject. The pressure line transmits the pressure at the mouthpiece back through 0.125 inch inner diameter tubing to a pressure transducer (Freescale Semiconductor, Chandler Ariz., MPX2010DP). That pressure transducer reports to custom written software in LabView via a multifunction data acquisition device after amplification by a custom operational amplifier circuit. The computer then uses those pressure measurements to adjust inhalation and exhalation pump speeds, overcoming the resistance of 25 feet of 0.25 inch tubing. The inhalation line and exhalation line connect to large peristaltic pumps (Cole Parmer, Chicago Ill., Masterflex PP Digital Drive). The computer also controls valves (VICI Valco Instruments, Houston Tex., Model C45) that select the input gas or output flow for recapture or to vent to room air. Gases are kept at ambient pressure in bags filled before the experiment with low loss circuits to ensure that any error during the experiment will not result in the loss of large volumes of pressurized $^{17}O_2$ gas.

Modeling of Inhaled Atomic Percentage of $^{17}O_2$ During the First Minute.

It is necessary to know or model the atomic percentage of $^{17}O$ in the oxygen metabolized by cells because while the $mH_2^{17}O$ rate of formation is measureable by MRI, the fractional enrichment of the $^{17}O_2$ generating that water at the cellular level during that time is not known. This is not as much of a problem for small animals that breathe very rapidly and therefore equilibrate their lung gas with the inhaled gas rapidly. A simple step-wise model was generated for estimating the fractional enrichment, fa(i), of $^{17}O$ in the lungs for each breath. Each step (breath) is modeled as an instantaneous inhalation, mixing of $^{17}O_2$ in the lungs, and exhalation via a simple dilution model with the addition of $O_2$ uptake into the body from the lungs. This is described by the following equation, $$f_a(i) = \frac{\overbrace{TV \cdot fiO_2 \cdot \alpha}^{A} + \overbrace{FRC \cdot (feO)_2 \cdot f_a(i-1)}^{B}}{\underbrace{(TV + FRC) \cdot fmO_2}_{C}} \quad [\text{Eq. 1}]$$

where TV is the tidal volume, $fiO_2$ is the fraction of all oxygen in the gas inspired, $feO_2$ is the expired fraction of all oxygen in the expired gas, $fiO_2$ is the fractional enrichment of $^{17}O$ in the gas inhaled, FRC is the functional residual capacity, is the fractional enrichment of $^{17}O$ in the prior step, and $fmO_2$ is the overall lung fraction of $O_2$ immediately after a breath—a weighted average of the $fiO_2$ and $feO_2$ above based on TV and FRC (Eq. A4, below). The piece of the equation labeled A represents an incoming breath and the piece labeled B accounts for the uptake of oxygen into the body from the lungs. The part labeled C normalizes the equation to units of fractional enrichment.

The derivation of Eq. 1 is as follows, beginning with an incoming volume of $^{17}O$, O, $Vi^{17}O$, described by Eq. A1.

$$Vi^{17}O = TV \cdot fiO_2 \cdot \alpha \quad [\text{Eq. A1}]$$

This volume adds to the $^{17}O$ left in the lungs at the end of the previous exhalation, $Ve^{17}O$, described by Eq. A2.

$$Ve^{17}O = FRC \cdot feO_2 \cdot f_a(i-1) \quad [\text{Eq. A2}]$$

To calculate $feO_2$ one must approximate the amount of oxygen consumed during the breath. For simplicity it is assumed that the inhalation, mixing, and exhalation happen instantly to produce a step change and the oxygen consumption occurs on the post-exhaled gas. This is given on a per breath basis by:

$$fcO_2 = \frac{VO_2}{RR} \frac{1}{FRC} \quad [\text{Eq. A3}]$$

where $fcO_2$ is the fraction of $O_2$ consumed from the exhaled lung volume during each breath. This leads to Eq. 2 where the oxygen expired is the oxygen inspired minus what was used by the body at steady state. The incoming tidal volume of $O_2$ mixes with the lung end exhalation volume, FRC, described by Eq. A1 and Eq. A2 to create the $fmO_2$, the mixed fraction of $O_2$.

$$fmO_2 = \frac{(TV \cdot (fiO_2) + (FRC \cdot (feO)_2)}{FRC + TV} \quad [\text{Eq. A4}]$$

The combination of all these equations leads to Eq. 1 restated at the end. The numerator in the equation specifies the volume of $^{17}O$ while the denominator specifies the overall volume of oxygen. To convert $fmO_2$ to the overall volume of $O_2$ in the denominator, it must be multiplied by the total volume TV+FRC.

$$f_a(i) = \frac{TV \cdot fiO_2 \cdot \alpha + FRC \cdot (feO)_2 \cdot f_a(i-1)}{(TV + FRC) \cdot fmO_2} \quad [\text{Eq. 1}]$$

The $fO_2$ just before inhalation, $feO_2$, is described by the following equation, $$feO_2 = fiO_2 - \frac{\dot{V}O_2}{RR} \frac{1}{FRC} \quad [\text{Eq. 2}]$$

where $Vo_2$ is the per minute consumption of $O_2$ and RR is the respiratory rate in breaths per minute. This equation gives the partial pressure of oxygen after body consumption. Using this model, the first minute of $^{17}O_2$ consumption was simulated according to the parameters shown in Table 1, below.

TABLE 1

| | Description | Value (Ref) | Unit |
|---|---|---|---|
| TV | Tidal Volume | 18 | mL/kg |
| $fiO_2$ | Inhaled fraction of oxygen | 0.20 | |
| α | Fractional enrichment of inhaled $^{17}O_2$ | 0.7 | |
| FRC | Functional Residual Capacity | 50 (*) | mL/kg |
| $VO_2$ | Whole body $O_2$ consumption | 5 (**) | mL/kg/min |
| RR | Respiratory Rate | 6 | breaths/min |

References:
(*) Mutoh T, Lamm W J, Embree L J, Hildebrandt J, Albert R K. Volume infusion produces abdominal distension, lung compression, and chest wall stiffening in pigs. J Appl Physiol 1992; 72(2): 575-582
(**) McKirnan M D, White F C, Guth B D, Longhurst J C, Bloor C M. Validation of a respiratory mask for measuring gas exchange in exercising swine. J Appl Physiol 1986; 61(3): 1226-1229; Willford D C, Hill E P, White F C, Moores W Y. Decreased critical mixed venous oxygen tension and critical oxygen transport during induced hypothermia in pigs. J Clin Monit 1986; 2(3): 155-168.

Figure 6:
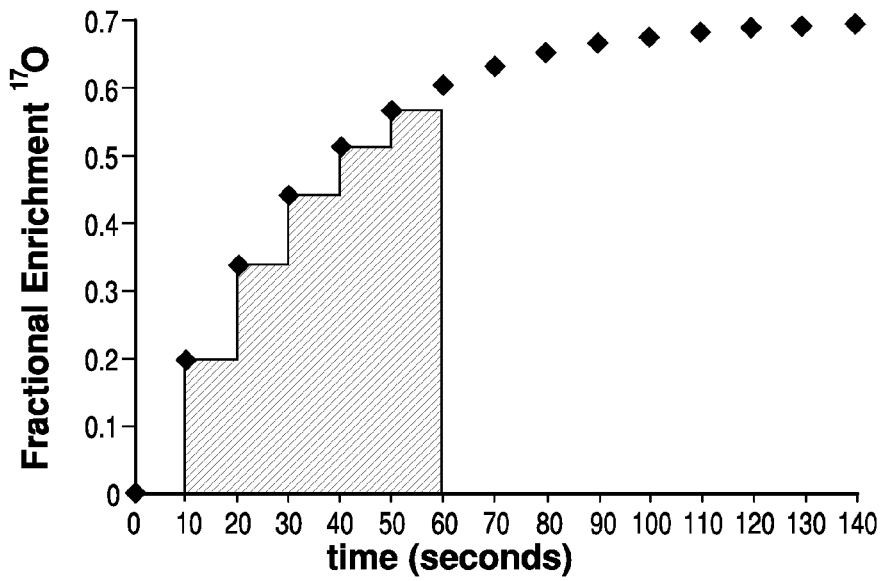
FIG. 6 provides a plot of a step function simulation of tissue $^{17}O$ fractional enrichment in oxygen gas when 15 breaths of 20% oxygen at 70% $^{17}O$ enrichment is given to a pig with the parameters in table 1, infra.

The results of this simulation, the fractional enrichment of the $^{17}O$ in the tissue after each breath, are shown in FIG. 6. The time of delivery for the $CMRO_2$ estimates herein is 6 breaths (1 minute), but data out to 15 breaths is shown to demonstrate the time to asymptote at the delivered enrichment. Delivery of gas begins at time 0, but a 10 second delay is given for breathing circuit delay, mixing time, and uptake and transport time of oxygen to the brain. The average of the area shaded in grey under the step function is used as f for computing $CMRO_2$ in Eqs. 6 and 7.

From the average of points at 10 seconds through 59 seconds, these simulations estimate a mean of 63.58% of the delivered gas concentration being metabolized during the $CMRO_2$ calculation time. The calculated average fractional enrichment at the tissue over the time of analysis is termed f.

Determination of $CMRO_2$ after $^{17}O_2$ Inhalation.

The theory for calculation of $CMRO_2$ based on $^{17}O_2$ is derived from flow measurements originally proposed by Kety & Schmidt (Kety S S, Schmidt C F. *The Nitrous Oxide Method For The Quantitative Determination Of Cerebral Blood Flow In Man: Theory, Procedure And Normal Values. J Clin Invest* 1948; 27(4):476-483) and later applied to $^{17}O$ (Zhang N, Zhu X H, Lei H, Ugurbil K, Chen W. *Simplified methods for calculating cerebral metabolic rate of oxygen based on 17O magnetic resonance spectroscopic imaging measurement during a short 17O2 inhalation. J Cereb Blood Flow Metab* 2004; 24(8):840-848; Fiat D, Kang S. *Determination of the rate of cerebral oxygen consumption and regional cerebral blood flow by non-invasive 17O in vivo NMR spectroscopy and magnetic resonance imaging: Part 1. Theory and data analysis methods. Neurol Res* 1992; 14(4):303-311). As a brief summary, $CMRO_2$ (µmol/g brain tissue/min) may be solved from:

$$\frac{d}{dt}C_b(t) = \frac{2\alpha(t)}{f_1}(CMRO_2) + Q[C_a(t) - C_v(t)] \quad [\text{Eq. 3}]$$

where $C_b(t)$ is the $mH_2^{17}O$ concentration of brain water in µmol/g water, $f_1$ is the weight fraction of water in tissue (g water/g tissue), $\alpha(t)$ is the fractional enrichment of metabolized $^{17}O_2$, Q is the blood flow rate of that area of tissue, and $C_a(t)$ and $C_v(t)$ are the arterial and venous $mH_2^{17}O$ concentrations respectively. There is a natural abundance of $H_2^{17}O$ in naturally occurring water (20.35 µmol/g), but we assume that is constant throughout the time of the experiment and all change is due to metabolic production. The first part of the equation represents locally produced $mH_2^{17}O$ while the second part represents outflow and inflow of $mH_2^{17}O$. In the short time course of $^{17}O_2$ measurement where there is not significant recirculation of $mH_2^{17}O$, $C_a(t)-C_v(t)$ approximates 0 during the measurement time. This is a common assumption in the $^{17}O$ and $^{15}O$ PET literature. One could suggest based on the venous lag time that $C_a(t)-C_v(t)$ is actually less than 0 during the measurement time, i.e., that venous outflow is greater than arterial input during the first minute, so this approximation may actually underestimate metabolism somewhat. Still, integration of Equation 3 with this simplification is shown:

$$\Delta C_b = \int_{t_o}^{t} \frac{2\alpha(t)}{f_1}(CMRO_2) \quad [\text{Eq. 4}]$$

where $\Delta C_b$ is the change in $mH_2^{17}O$ concentration over the time of $t_0$ to t, the time of the $CMRO_2$ calculation. Equation 4 can then be reduced to Eq. 5 below.

$$CMRO_2 = \frac{\Delta C_b f_1}{2f} \quad [\text{Eq. 5}]$$

As in the previous section, $\alpha(t)$ cannot simply be approximated by $\alpha$, and instead is replaced by the average enrichment over the time of $CMRO_2$ calculation, f. The amount of water generated per minute can now be solved from the normalized indirect signal change, $S/S_0$, by the equation for finding the concentration of a $T_{1\rho}$ contrast agent normalized by the fractional enrichment of $^{17}O$ (Stolpen A H, Reddy R, Leigh J S. *17O-decoupled proton MR spectroscopy and imaging in a tissue model. J Magn Reson* 1997; 125(1):1-7), f, absorbed over that first minute described by Eq. 1 in the section above.

$$\Delta C_b = \frac{-\ln(S/S_0)}{TSL \cdot R_{1\rho}} \quad [\text{Eq. 6}]$$

In Eq. 6, TSL is the sum of the $T_{1\rho}$ preparation time and the time to the first (center line of k-space) echo time (TE) and the constant $R_{1\rho}$, the relaxation enhancement of tissue due to $H_2^{17}O$, was set to $5.91*10^{-6}$ (µmol/g water)$^{-1}$ ms$^{-1}$ based on measurements made in tissue phantoms (Id.), which closely approximates $R_2$ (Reddy R, Stolpen A H, Leigh J S. *Detection of 17O by proton T1 rho dispersion imaging. J Magn Reson B* 1995; 108(3):276-279). Combining Eq. 5 and Eq. 6 yields the final equation used to calculate CMRO2 for indirect imaging in Eq. 7.

$$CMRO_2 = \frac{-\ln(S/S_0)f_1}{TSL \cdot R_{1\rho} \cdot 2f} \quad [\text{Eq. 7}]$$

For direct $^{17}O$ spectroscopy, the change in signal is directly proportional to the change in water concentration of $mH_2^{17}O$, leading to eq. 8 as follows:

$$CMRO_2 = \frac{(S/S_0)f_1}{2f} \quad [\text{Eq. 8}]$$

where $S_0$ is assumed to be the natural abundance signal of $^{17}O$ and $f_1$ is set to 0.77 (Herscovitch P, Raichle M E. *What is the correct value for the brain—blood partition coefficient for water? J Cereb Blood Flow Metab* 1985; 5(1):65-69). The cerebral metabolic rate of oxygen consumption is calculated from the first 50 seconds of oxygen inhalation, after a 10 second delay. This delay is due to the delay in signal change, as expected between the start of inhalation and cellular conversion to water due to breathing circuit delay, mixing time, and uptake and transport time of oxygen.

Animal Experiments.

All animal experiments were approved by the Institutional Animal Care and Use Committee. Pigs weighing 19 kg to 41 kg were used. Induction of anesthesia was performed by an initial IM injection of ketamine 22 mg/kg, xylazine 0.025 mg/kg, and atropine 0.05 mg/kg and maintained with ketamine 60 mg/kg/hr and diazepam 2 mg/kg/hr. Animal heart rate and oxygen saturation were monitored with a standard infrared pulse-oximeter and full oxygen saturation (98-100%) without fluctuation was required for the experiments to proceed. All experiments begin with $T_1$-weighted sequence for localization and anatomical imaging of the brain.

Magnetic Resonance Imaging.

Direct imaging was performed on a broadband-enabled 3T Siemens Trio scanner. Proton images were taken with the body coil and then without moving the pig, a custom built interface was connected to the scanner and interfaced with a home built 9 cm surface coil tuned to 16.71 MHz placed on top of the pig's head. Calibration of the rectangular pulse used was performed by taking a number of gradient recalled echo images and maximizing signal-to-noise over the brain region. One $^{17}O$ image was taken in each plane. Parameters were as follows: repetition time (TR) 100 ms, TE 1.8 ms, field of view (FoV) 40×40 cm, 64×64 matrix, bandwidth 200 Hz/Pixel, asymmetric echo. Following that a series of pulse acquire spectra were taken with the same hard pulse over 15 minutes. Pulse acquire parameters were: TR 100 ms, 256 points, two step phase cycling, 40 kHz bandwidth, repeated 9000 times over 15 minutes.

Figure 7:
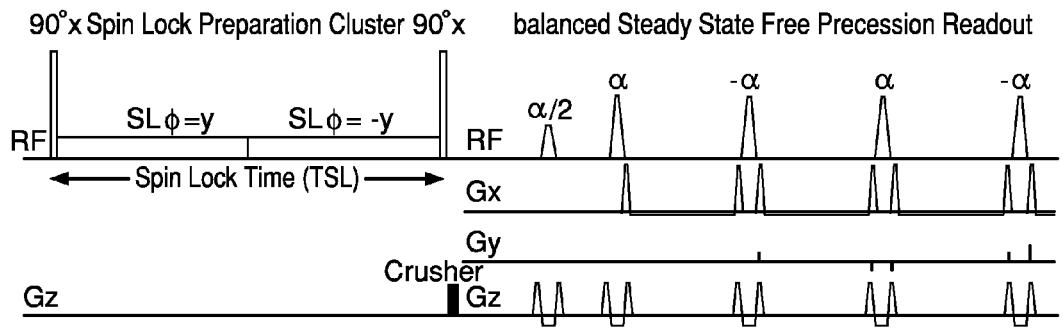
FIG. 7 shows the spin lock prepared balanced steady state free precession readout used to estimate $CMRO_2$.

Indirect imaging was performed on separate occasions on a 1.5T Siemens Sonata scanner. Images were taken with a 15 cm vendor supplied surface coil placed on the head of the pig. Serial images during room air and $^{17}O_2$ delivery were taken with a $T_{1\rho}$-prepared single-shot, high flip angle, centrically encoded, fully-balanced gradient echo sequence reported shown in FIG. 7. A more thorough treatment of this sequence and its use to detect $mH_2^{17}O$ in vivo are presented in a separate manuscript (Mellon E A, Beesam R S, Kasam M, Baumbardner J E, Borthakur A, Witschey W R Jr., Reddy R. *Single shot T1(rho) magnetic resonance imaging of metabolically generated water in vivo. Adv Exp Med Biol* 2008; in press). Parameters were: TR 9.7 ms, TE 4.7 ms, slice thickness 6 mm, FoV 200 mm$^2$, 128×128 matrix, bandwidth 130 Hz/Pixel, flip angle 180° (opening pulse 90°), spin locking amplitude 100 Hz, spin locking time 75 or 200 ms, fat saturation on, time per image 1.6 seconds, 2 second delay for $T_1$ recovery.

Arterial Blood Sampling and $^{17}O$ NMR Spectroscopy of Blood.

During imaging, arterial blood sampling was performed on several occasions. An optimized protocol was developed and repeated. An arterial catheter was placed under ultrasound guidance into the femoral artery in the large animal fluoroscopy suite. Approximately 2 cc of blood was collected over 3-5 seconds into each Vacutainer Serum Separator Tube (Becton-Dickinson, #367983) at a rate of one sample each 10 seconds for the first 12 samples and then 60 seconds each for six more samples. Four control samples were taken before the experiment began. The tubes used are designed to reseal immediately after needle puncture. Their ability to remain sealed was tested by taking several tubes at random, creating a strong negative pressure inside the tube with a vacuum pump attached to a needle, and then repeated puncture with larger diameter needles than used for blood sampling. The pressure inside the tubes was checked after over a dozen punctures and had changed less than 10%. Storage over a period of a week of a sampling of tubes showed no depressurization over time.

A concern is that water $^{17}O$ will exchange with ambient $CO_2$ through bicarbonate ion, a very fast reaction when catalyzed by carbonic anhydrase as in whole blood (Mills G A, Urey H C. *The Kinetics of Isotopic Exchange between Carbon Dioxide, Bicarbonate Ion, Carbonate Ion and Water. J Am Chem Soc* 1940; 62 (5):1019-1026). To minimize this effect, serum was separated by centrifugation soon after the experiment. Tubes were then frozen at −20 C and kept sealed until the time of analysis. Centrifugation places a gel between the serum and red blood cells in these tubes to fully separate the two. This procedure serves to protect the samples in two ways. First, because the tube is sealed, blood can mix only with the small amount of $CO_2$ (~450 parts per million) in the small amount of air (<1 mL) drawn into the tube, a trivial source of mixing. A small amount of mixing can occur with the blood bicarbonate, but this reaction is extremely fast and occurs in the body regardless. As blood bicarbonate is <30 mM (Recchia F A, Vogel T R, Hintze T H. *NO metabolites accumulate in erythrocytes in proportion to carbon dioxide and bicarbonate concentration. Am J Physiol Heart Circ Physiol* 2000; 279(2):H852-856), this represents a trivial loss of $^{17}O$. Second, carbonic anhydrase has almost no activity in serum (Meldrum N U, Roughton F J. *Carbonic anhydrase. Its preparation and properties. J Physiol* 1933; 80(2):113-142). So when the serum is re-exposed to air, the reaction catalyst is missing, and the NMR measurement completed within 10 minutes suggests that the loss of $^{17}O$ is less than 5% during that time (Bitterman N, Lin L, Forster R E. *A micromethod for measuring carbonic anhydrase activity using 18O exchange between CO2 and H2O. J Appl Physiol* 1988; 65(4):1902-1906).

An 11.7T Bruker DMX400 Avance Spectrometer equipped with a 1H/X nucleus decoupler probe tuned to $^{17}O$ was used to measure 1 mL of each sample loaded into 5 mm ID NMR tubes just before analysis. Spectra were recorded without lock at room temp. Five samples taken before the start of the experiment comprise the data point at time 0, assumed to be the natural abundance of $H_2^{17}O$, with a standard deviation of 0.17 μmol/g serum. The parameters for $^{17}O$ spectroscopy were: TR 41 ms, 4096 points, bandwidth 50 kHz, 4000 averages, flip angle 90°.

Data Analysis.

For the direct measurement of $mH_2^{17}O$ production, the integrals of the pulse acquire spectra from 4 averages per data point (400 ms each) were normalized to the natural abundance. The signal trace during $^{17}O_2$ delivery was fit linearly over 50 seconds beginning 10 seconds after the start of the $^{17}O_2$ pulse to generate the $mH_2^{17}O$ production in Table 1. The slope and standard error of the linear fit was used in Eq. 8 as S. The plots of the direct signal change were temporally smoothed over 16 seconds before and after to show the trend in signal change.

For indirect measurement of $CMRO_2$, region of interest analyses were performed by segmenting each half of the pig brain without including ventricles based on anatomical contrast images and a pig brain anatomy atlas. The time course of each ROI in the indirect imaging was temporally smoothed over 16.2 seconds (4 points) before and after to filter high frequency noise. A linear fit was performed over 50 seconds approximately 10 seconds after the start of the $^{17}O_2$ pulse, and the slope of that line was used to estimate the signal change and fitting error per minute.

Results.

Figure 8:
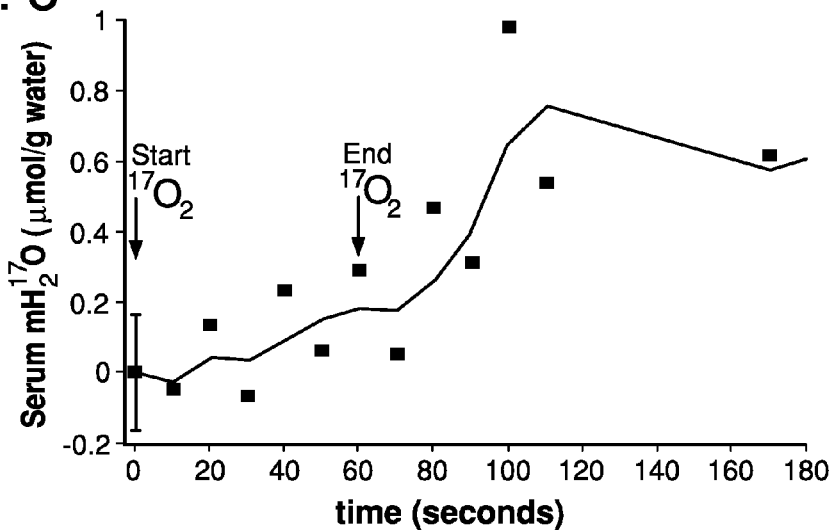
FIG. 8 provides the results of a serial arterial blood sampling experiment during and after 1 minute of $^{17}O_2$ delivery.

Blood sampling was performed during scanning on two separate occasions. The delay between the start of $^{17}O_2$ delivery and the start of wash-in, defined as two successive points over the standard deviation of the measurement, is shown in FIG. 8 to be about 90 seconds in the 40.8 kg pig. As provided in FIG. 8, delivery of $^{17}O_2$ as 80% $N_2$/20% $O_2$ (70% $^{17}O$ enriched) begins at time 0 seconds and ends at 60 seconds as in all the following figures. Serum concentration of $H_2^{17}O$ was calculated by integrating the $H_2^{17}O$ peak obtained by $^{17}O$ spectroscopy of the blood samples taken at the given time points. The solid line is a 2 point moving average of the data points. The first data point is an average of 5 samples taken before the start of $^{17}O_2$ delivery, assumed to be 20.35 μmol $H_2^{17}O$/g water. The error bar is the standard deviation of those 5 points of 0.17 μmol/g. A second experiment showed the delay to be on the order of 70 seconds in a 19.8 kg pig (data not shown).

Figure 9:
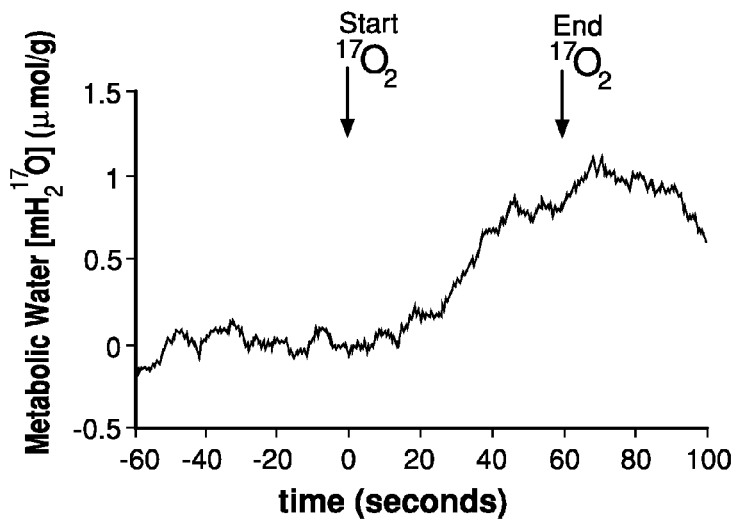
FIG. 9 shows time series spectra plotting $H_2^{17}O$ peak integrals over time to indicate $\mu$ mol $H_2^{17}O$/g water.

FIG. 9 shows time series spectra plotting $H_2^{17}O$ peak integrals over time to indicate μ mol $H_2^{17}O$/g water.

Figure 10:
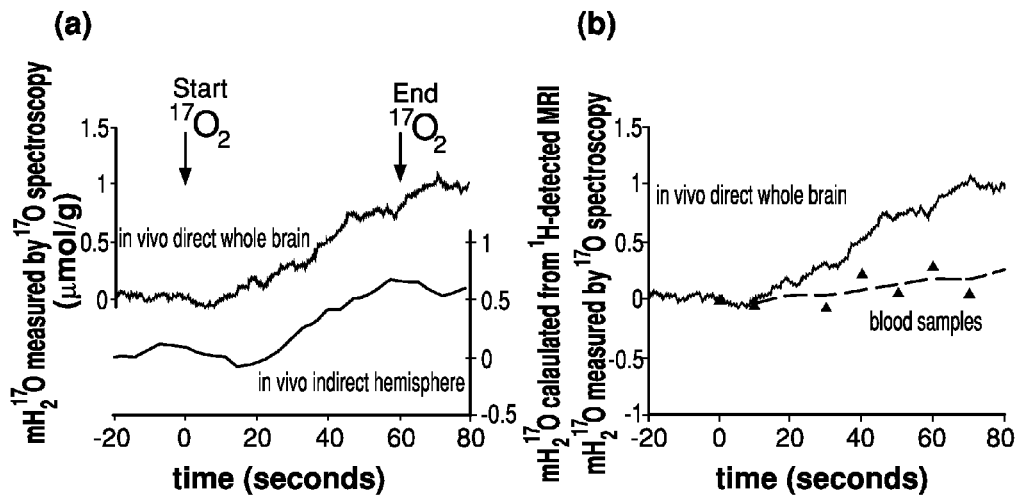
FIG. 10a presents the metabolic water change measured by separate experiments using direct $^{17}O$ spectroscopy and proton-detected $H_2^{17}O$ to show the similarity in vivo.
FIG. 10b demonstrates the rise in metabolic water from brain without a concurrent rise in recirculated metabolic water. The difference between the two lines indicates the $CMRO_2$.

The correlation of indirect and direct imaging is shown in FIG. 10a. Excellent agreement between the indirect and direct signals verifies the specificity of the current methods. The indirect signal is converted to concentration of $mH_2^{17}O$ by Equation 6. FIG. 10b shows the time series plot of blood sampling in FIG. 8 combined with direct imaging shown in FIG. 9. The difference between the two lines indicates the $CMRO_2$. Since the difference between them is so great, the recirculation can be effectively ignored.

Figure 11:
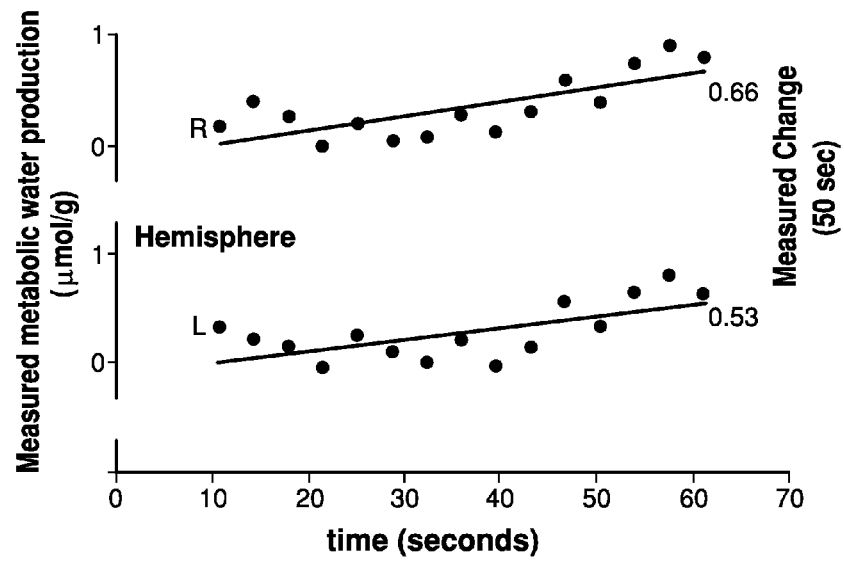
FIG. 11 shows an example of hemispheric changes (Right and Left) in water production used to generate $CMRO_2$ estimates in the swine listed in Table 2, infra.

FIG. 11 demonstrates the changes in $mH_2{}^{17}O$ post $^{17}O_2$ delivery during the first 60 seconds and shows the linear fit to the data points used to calculate $CMRO_2$. Shown is the data for pig 2, representative of the data for the other swine. The slope of the signal change in half of the brain in one central slice of brain gives the hemispheric $mH_2{}^{17}O$ production and that is calculated for each hemisphere in Table 2 (below) and converted to $CMRO_2$ measurements. The f values correspond to the fractional enrichment of $^{17}O$ delivered where 0.41 corresponds to delivery of 70% $^{17}O_2$ and 0.24 corresponds to delivery of 40% $^{17}O_2$. Taken together, these demonstrate that CMRO2 can be calculated by the signal change of 1 minute of inhalation by the indirect technique at 1.5 Tesla.

TABLE 2

Estimated cerebral metabolic rates of oxygen consumption ($CMRO_2$)

| Direct $^{17}O$ | f | $f_1$ | $CMRO_2$ µmol/g/min | $CMRO_2$ error |
|---|---|---|---|---|
| Pig 1 Whole Brain | .41 | .77 | 1.19 | 0.43 |
| Indirect $^{17}O$ | | TSL | | |
| Pig 2 Left Hemisphere | .24 | 205 | 1.03 | 0.33 |
| Pig 2 Right Hemisphere | .24 | 205 | 1.30 | 0.26 |
| Pig 3 Left Hemisphere | .24 | 205 | 1.49 | 0.39 |
| Pig 3 Right Hemisphere | .24 | 205 | 1.63 | 0.62 |
| Pig 4 Left Hemisphere | .41 | 80 | 0.88 | 0.52 |
| Pig 4 Right Hemisphere | .41 | 80 | 1.46 | 0.7 |
| Pig 5 Left Hemisphere | .41 | 80 | 1.34 | 0.33 |
| Pig 5 Right Hemisphere | .41 | 80 | 1.54 | 0.59 |

Indirect Average 1.33 ± 0.26

Discussion.

The $CMRO_2$ of pigs of comparable size using a similar continuous infusion ketamine and benzodiazepine anesthesia regimen has been estimated to be 1.63±0.19 µmol/g/min by $^{15}O$ PET (Poulsen P H, Smith D F, Ostergaard L, Danielsen H, Gee A, Hansen S B, Astrup J, Gjedde A. *In vivo estimation of cerebral blood flow, oxygen consumption and glucose metabolism in the pig by [15O] water injection, [15O] oxygen inhalation and dual injections of [18F] fluorodeoxyglucose. J Neurosci Methods* 1997; 77(2): 199-209). The spatial resolution of those measurements presented here is the same as those $^{15}O$ PET images without the need for an onsite cyclotron or radioactivity. Still, differences in pig $CMRO_2$ found in the literature vary significantly depending on the technique, anesthesia regimen, and size of pig used. One study averages 1.20±0.29 µmol/g/min and 1.15±0.46 µmol/g/min by radioactive and fluorescent microspheres respectively (Ehrlich M P, McCullough J N, Zhang N, Weisz D J, Juvonen T, Bodian C A, Griepp R B. *Effect of hypothermia on cerebral blood flow and metabolism in the pig. Ann Thorac Surg* 2002; 73(0:191-197). Another radioactive microsphere study in pigs of different ages found $CMRO_2$ ranging from 1.30 to 1.75 µmol/g/min (Ichord R N, Kirsch J R, Helfaer M A, Haun S, Traystman R J. *Age-related differences in recovery of blood flow and metabolism after cerebral ischemia in swine. Stroke* 1991; 22(5):626-634). The measurements made here compare favorably to these values.

While 3 Tesla scanners are relatively widespread clinically, lower fields have some advantages in the indirect imaging application. The J-coupling interaction that leads to relaxation enhancement is a field strength independent interaction. As such, higher starting $T_2$ values for tissue make the absolute $T_2$ reduction by $H_2{}^{17}O$ greater at lower field strengths. Also, lower tissue $T_1$ values allow for faster averaging of the spin-spin coupling based $H_2{}^{17}O$ effect. Further, diminished magnetic susceptibility effects reduce the competing signal changes from cerebral blood and sequence artifacts. This is in contrast to $^{17}O$ which benefits from ultra-high fields and is typically performed at clinically unavailable field strengths. For all these reasons 1.5 T was chosen for the present studies.

Nevertheless, the major technical limitation of $^1H$ detected $^{17}O$ imaging is the relatively small effect of physiologic levels of $^{17}O$ on $^1H$ relaxation. This problem can be overcome in human applications for several reasons. First, the $CMRO_2$ measured here is on the order of 3-fold less than the $CMRO_2$ of resting humans, mostly due to anesthesia. Therefore human studies should correspond to a roughly 3× improvement of the $^{17}O$ effect. Second, the human brain is so much larger than pig brain that region of interest analyses should be more easily obtainable and more meaningful. Third, as humans are far more cooperative than pigs and do not require anesthesia, human studies should be easier to perform. Further, as units of $^{17}O$ will cost less as more is produced, it is hoped that the cost of these techniques will be improved by increased interest and usage by the research community.

It must be noted that the equations used to quantify $CMRO_2$ have sources of potential error for absolute measurements. The value of the relaxation enhancement due to $^{17}O$ on $^1H$, $R_2$, for example is difficult to measure in vivo or with ex vivo tissues, and as such it may be imprecise. As well, $R_2$ may vary based on different tissue parameters such as grey or white matter or cerebral blood volume per voxel. For example, the sequence given in this paper measures $R_{1\rho}(100$ Hz) as $1.37*10^{-5}$ $mM^{-1}$ $ms^{-1}$ in $H_2{}^{17}O$ doped phosphate buffered saline phantoms, and that would likely approximate the value for blood or cerebrospinal fluid. It is also known that $R_2$ has a dependence on pH (Meiboom S. *Nuclear Magnetic Resonance Study of Proton Transfer in Water. Journal of Chemical Physics* 1961; 34(2):375-&). This is a very minor concern for application in cerebral infarction, as one rat model shows overall tissue pH in hyperacute stroke leading to complete infarction to drop to a minimum of 6.6 (Nedergaard M, Kraig R P, Tanabe J, Pulsinelli W A. *Dynamics of interstitial and intracellular pH in evolving brain infarct. Am J Physiol* 1991; 260(3 Pt 2):R581-588) and $R_2$ shown by Meiboom only varies about 10% over the pH interval 6.2-7.8. Also, since $R_2$ is reduced by pH extremes, further drops in pH would underestimate $mH_2{}^{17}O$ production and serve to magnify the probability that a tissue is infracted in future applications of this technology. The value off, the tissue fractional enrichment of $^{17}O$, chosen is based from a very simple, approximate model of inhalation appropriate for averaging over several breaths; however more sophisticated modeling could potentially be used. This factor has not been considered in the estimation of $CMRO_2$ with $^{17}O_2$ previously because small animals have high respiratory rates and the slurring of the $^{17}O$ fractional enrichment may be neglected because gas mixing in the lungs occurs much more quickly. Also, it becomes more reasonable to neglect f with longer time periods of inhalation where the fractional enrichment has had sufficient time for equilibration with the enriched $^{17}O$ gas.

Despite these considerations, relative $CMRO_2$ in the same subject or across subjects can be estimated using the current techniques.

The $T_{1\rho}$-prepared, centrically encoded, fully balanced spin echo sequence used in this study evolved from decoupling experiments in which high $T_{1\rho}$ spin lock amplitudes (Rizi R, Charagundla S R, Song H K, Reddy R, Stolpen A H, Schnall M D, Leigh J S. *Proton T1rho-dispersion imaging of rodent brain at 1.9 T. J Magn Reson Imaging* 1998; 8(5): 1090-1096), off resonance spin-locking (Charagundla S R, Stolpen A H, Leigh J S, Reddy R. *Off-resonance proton T1rho dispersion imaging of 17O-enriched tissue phantoms. Magn Reson Med* 1998; 39(4):588-595), or $^{17}O$ decoupling (Reddy R, Stolpen A H, Charagundla S R, Insko E K, Leigh J S. *17O-decoupled 1H detection using a double-tuned coil. Magn Reson Imaging* 1996; 14(9):1073-1078) are used to mitigate the $^1H$—$^{17}O$ J-coupling interaction. This sequence improves the temporal resolution for these decoupling techniques significantly by allowing them to be performed with a fast single shot imaging readout. This brings down the temporal resolution from at least 10 seconds per image with turbo spin echo based readouts to about 3.5 seconds with the current sequence and parameters. The small spin lock amplitude, 100 Hz, used here gives extremely similar $R_{1\rho}$ constants to measured $R_2$ in the case of $^{17}O$ (Stolpen A H, Reddy R, Leigh J S. *17O-decoupled proton MR spectroscopy and imaging in a tissue model. J Magn Reson* 1997; 125(1):1-7; Reddy R, Stolpen A H, Leigh J S. *Detection of 17O by proton T1 rho dispersion imaging. J Magn Reson B* 1995; 108(3):276-279) without visible artifact or effect of macroscopic background field gradients. This study was performed with a body coil transmitter and surface receiver, which is suggested for the high homogeneity of the body coil for spin-locking Decoupling of the $^1H$—$^{17}O$ interaction can be performed with high spin lock amplitudes as well. While decoupling is not performed in this study due to implementation difficulties and specific absorption rate concerns on clinical scanners, decoupling experiments similar to those previously conducted (Reddy R, Stolpen A H, Leigh J S. *Detection of 17O by proton T1 rho dispersion imaging. J Magn Reson B* 1995; 108(3): 276-279; Reddy R, Stolpen A H, Charagundla S R, Insko E K, Leigh J S. *17O-decoupled 1H detection using a double-tuned coil. Magn Reson Imaging* 1996; 14(9):1073-1078) can be performed using the sequence and delivery techniques presented here. Also, it may be possible that the same estimates could be made with a fast $T_2$ weighted sequences such as spin echo echo planar imaging or single shot turbo spin echo methods. In particular, spin echo echo planar imaging presents the possibility of obtaining 3D metabolic images. However, caution must be exercised using sequences, as any possible distortion or artifact may mask the small proton signal change generated by physiologic short-term $mH_2{}^{17}O$ production. $T_{1\rho}$ imaging, as shown here, enables us to measure the small changes due to $mH_2{}^{17}O$ that may not be seen with other sequences due to artifacts that may obscure small signal changes in long $T_2$-weighted images or in echo planar imaging.

While it is recognized that the anesthesia regimen may change the vascular recirculation of $mH_2{}^{17}O$ as opposed to awake humans, multiple $^{15}O$ PET studies have modeled the time course of recirculation for metabolic water using similar time courses with a single breath hold in humans and these have also made $CMRO_2$ measurements claiming recirculation during the first minute to be negligible (Meyer E, Tyler J L, Thompson C J, Redies C, Diksic M, Hakim A M. *Estimation of cerebral oxygen utilization rate by single-bolus 15O2 inhalation and dynamic positron emission tomography. J Cereb Blood Flow Metab* 1987; 7(4):403-414; Ohta S, Meyer E, Thompson C J, Gjedde A. *Oxygen consumption of the living human brain measured after a single inhalation of positron emitting oxygen. J Cereb Blood Flow Metab* 1992; 12(2):179-192). Indeed, the measurements made here and the modeling used for $CMRO_2$ measurement is very similar to $^{15}O$ experiments performed in humans (Mintun M A, Raichle M E, Martin W R, Herscovitch P. *Brain oxygen utilization measured with O-15 radiotracers and positron emission tomography. J Nucl Med* 1984; 25(2):177-187). In that study, 40 seconds were used to measure $CMRO_2$ after a 20 second delay after start of inhalation. Recirculation of $H_2{}^{15}O$ was measured and found to be minimal during that time. The error in $CMRO_2$ calculation ignoring wash-in was simulated to be less than 15% for very critically low values of oxygen extraction fraction (<0.15), and less than 5% for typical oxygen extraction fractions (>0.3). With the current data and the PET data taken together, it seems the recirculation delay is comparable in humans, and as such, anesthesia in pigs is not thought to be a significant factor for the kinetics of $mH_2{}^{17}O$ recirculation. If anything, these experiments should become easier to perform in humans who have larger brains, higher resting brain metabolic rates, and do not require anesthesia for imaging.

Another difference between the current study and many short time course PET studies is that for delivery PET studies frequently use a single tidal volume inhalation of tracer with a breath hold. We do not employ this strategy here for several reasons. First, any fluctuation in blood oxygen content results in a change in MRI signal (Butte D, Chiarelli P, Wise R, Jezzard P. *Measurement of cerebral blood volume in humans using hyperoxic MRI contrast. J Magn Reson Imaging* 2007; 26(4):894-899; Chiarelli P A, Butte D P, Wise R, Gallichan D, Jezzard P. *A calibration method for quantitative BOLD fMRI based on hyperoxia. Neuroimage* 2007; 37(3):808-820). A single bolus of 100% oxygen after breathing room air will cause an increase in MR signal that will interfere with the measurement (suggested by above references and demonstrated by EAM, data not shown). It is possible to have the subject breathe 100% oxygen for a period of time to stabilize the MR signal before $^{17}O_2$ delivery and this has been done by us with similar $mH_2{}^{17}O$ observations. However, modeling indicates that this wastes much more expensive $^{17}O_2$ gas by exhalation of oxygen unused by the lungs than the method presented here. This is because hemoglobin is fully saturated past ~15% $O_2$ at 1atm pressure and as such most of the oxygen in a 100% oxygen inhalation will not be absorbed. A large single breath of $^{17}O_2$ could potentially be held longer to decrease the amount of exhaled $^{17}O$, however this risks even small amounts of hemoglobin desaturation which will artificially enhance the $^{17}O$ effect by $T_2^*/T_2/T_{1\rho}$ reduction by paramagnetic venous deoxyhemoglobin. Still, with careful bolusing and hemoglobin saturation accounting, a single breath MRI method could be obtained that would use approximately the same amount of $^{17}O_2$ used here.

The present study demonstrates the feasibility of measuring $CMRO_2$ in large animals on clinical scanners using a single tidal volume of $^{17}O_2$ gas delivered with a precision delivery circuit. By minimizing gas required for $CMRO_2$ measurements, employing a large animal model, and utilizing clinical hardware, this represents a crucial first step towards the translation of small animal $^{17}O_2$ studies to humans. A simple model of lung mixing and delivery to tissues is presented. Arterial blood sampling and analysis of $mH_2{}^{17}O$ content shows the time when recirculation begins to be 60-80 seconds—ample time for fast imaging techniques to obtain numerous images for $CMRO_2$ estimation. High temporal resolution indirect and direct imaging is correlated to show similar results for the estimation of $CMRO_2$ non-invasively during those 60 seconds. For indirect imaging only a clinical 1.5T scanner with standard hardware and an easily programmable pulse sequence is necessary.

EXAMPLE

Single Shot $T_{1\rho}$ Magnetic Resonance Imaging of Metabolically Generated Water In Vivo As discussed above, the use of Oxygen-17 MRI provides great promise for the clinically-useful quantification of metabolism. To bring techniques based on $^{17}O$ closer to clinical application, demonstrated herein is imaging of metabolically generated $H_2{}^{17}O$ in pigs after $^{17}O_2$ delivery with increased temporal resolution $T_{1\rho}$-weighted imaging and precision delivery of $^{17}O_2$ gas. The kinetics of the appearance of $H_2{}^{17}O$ in pig brains are displayed with one to two minutes of $^{17}O_2$ delivery, the shortest delivery times reported in the literature. It is also shown that $H_2{}^{17}O$ concentrations can be quantified with single shot $T_{1\rho}$ imaging based on a balanced steady state free precession readout, and that with this strategy pausing to reduce $T_1$ saturation increases sensitivity to $H_2{}^{17}O$ over acquisition in the steady state. Several additional considerations with this sequence, which can be generalized to any pre-encoding cluster, such as energy deposition are considered.

Reported herein is single shot $T_{1\rho}$ imaging with readout based on $T_{1\rho}$-prepared balanced Steady State Free Precession (bSSFP). Pigs are used as a model for their similar lung capacities and circulations to humans. While the detection of $H_2{}^{17}O$ with a steady state sequence has been reported, the present study shows theoretically $H_2{}^{17}O$ sensitivity is improved by a sequence with a $T_{1\rho}$ or $T_2$ pre-encoding cluster followed by signal acquisition without the steady state directly after pre-encoding. The efficacy is demonstrated by phantom experiments and in vivo.

Methods.

Images were acquired from a Siemens 1.5T Sonata MR scanner. Simulations were performed with custom-written software in Matlab. The $T_{1\rho}$ pre-encoded bSSFP pulse sequence consists of a $T_{1\rho}$ preparatory cluster followed by a centrically-encoded 2D bSSFP readout without dummy scans (shown in FIG. 7).

Estimation of $T_{1\rho}$ in 17-Oxygen Water Phantoms.

The ability of the sequence to detect changes in $H_2{}^{17}O$ concentration was measured by imaging six 15 mL conical tubes filled with 1× Phosphate Buffered Saline doped with $H_2{}^{17}O$ (Isotec, Miamisberg, Ohio) in steps of 5 mM from 20 mM (natural abundance) to 45 mM. These tubes were sealed and placed into a 9 cm jar filled with water. A receive only loop coil was placed around the jar and used in combination with the body transmit coil. Cross-sectional images of the tubes were acquired with a spin lock amplitude of 100 Hz and spin lock times of 200, 400, 600, 800, and 1000 msec. Imaging parameters are: FoV 90 mm$^2$, ST 5 mm, TR/TE 10.4/5.2 ms, Matrix 128$^2$, BW 130 Hz/Px, α=180°.

The concentrations of the phantoms were determined experimentally according to the following equation:

$$f(p) = f_n + \left[\ln\left(\frac{S_{T_{1\rho},NA}}{S_{PD,NA}}\right) - \ln\left(\frac{S_{T_{1\rho},^{17}O}}{S_{PD,^{17}O}}\right)\right]\frac{1}{R_{1\rho} \cdot TSL} \quad \text{Eq. (1)}$$

Where fn is the natural abundance $[H_2{}^{17}O]$, S is the signal from a pixel or ROI with natural abundance (NA) $[H_2{}^{17}O]$ or $[H_2{}^{17}O]$ added ($^{17}O$) taken as a proton density weighted image to account for coil sensitivity or when $T_{1\rho}$ pre-encoded ($T_{1\rho}$). $R_{1\rho}$ is the relaxivity due to $H_2{}^{17}O$ and TSL is the spin lock time.

Animal Imaging.

The Institutional Animal Care and Use Committee of the University of Pennsylvania approved all animal experiments. A live pig was placed supine inside a 1.5T Siemens Sonata clinical scanner on a vendor supplied surface coil. Once placed inside, the intubation tube was connected to a custom precision delivery breathing circuit that drove the pig's breathing at 6 breaths/min at a tidal volume of 18 mL times the weight in kg. A standard T1-weighted localizer sequence was run to find a suitable coronal image of the middle portion of the pig brain that included cortex, brainstem, and ventricle. A T1-weighted IR-prepared GRE sequence (MP-RAGE) was performed to obtain anatomical images of the pig brain and the desired slice. Sequence parameters for the $T_{1\rho}$-prepared bSSFP are as follows: TR/TE 9.7/4.8 ms, ST 5 or 10 mm, FoV 200 mm$^2$, 128$^2$ matrix, BW 130 Hz/Px, α=180°, SL Amp 100 Hz, fat saturation on, 1.6 second readout time, 2 second delay between acquisition, time per image 3.6/sec.

Figure 12:
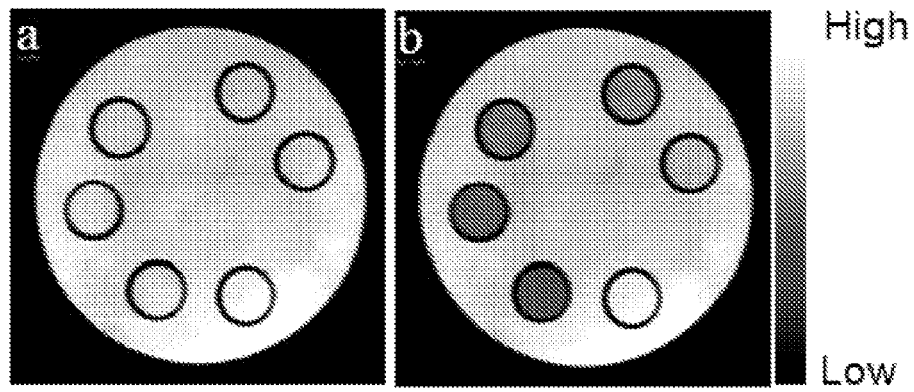
FIG. 12 and FIG. 13 show the results of the quantification of $[H_2^{17}O]$ is performed in phantoms and quantified using the relaxivity of $H_2^{17}O$ in PBS.
Figure 13:
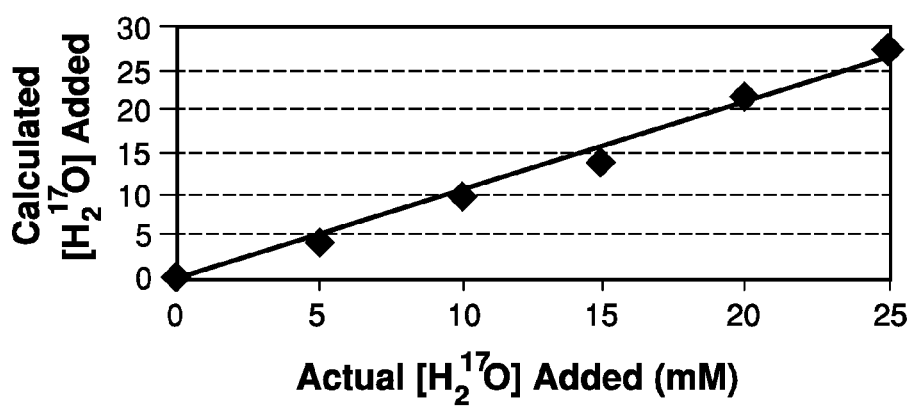

A demonstration of the $T_{1\rho}$-prepared bSSFP sequence shows that measurements of $H_2{}^{17}O$ concentrations can be made with single shot imaging very rapidly; FIGS. 12 and 13 show the results of the quantification of $[H_2{}^{17}O]$ is performed in phantoms and quantified using the relaxivity of $H_2{}^{17}O$ in PBS. FIG. 12 provides cross-sectional images of 15 mL conical tubes filled with phosphate buffered saline and doped with increasing amounts of $H_2{}^{17}O$ to concentrations from 20 mM (natural abundance) to 45 mM (25 mM added). The left image (a) shows the ordering of the phantoms (labeled by concentration) in a proton density image that uses only two 90 degree pulses and no spin locking as a preparation cluster. The image (b) shows the contrast developed with 100 Hz spin locking. The relaxivity of these phantoms taken from a series of $T_{1\rho}$-weighted images (not shown) was applied to equation 1 along with the signal intensities from the above images to calculate $^{17}O$ concentrations (FIG. 13).

To show that high SNR and contrast are maintained by using a sequence with a pre-encoding cluster versus detecting pure $T_2$ changes in the steady state, Bloch equation simulations were performed to show that detecting in the steady state gives less contrast and CNR than methods not in the steady state. In essence, by filling the center of k-space first with a high flip angle, contrast is much higher than when obtaining $T_2$ contrast in the steady state. The simulated differences are summarized in Table 3, below. Despite the possibility of generating images faster, steady state acquisition offers less SNR and CNR efficiency.

TABLE 3

|  | Steady State | Non-Steady State |
| --- | --- | --- |
| Equation | $M_{SS} = M_0 \dfrac{\sin(\alpha)}{1 + \cos(\alpha) + (1 - \cos(\alpha))(T_1/T_2)}$ | $M = M_0 \exp\left(\dfrac{-t}{T_2 \text{ or } T_{1\rho}(\omega)}\right)$ |
| Contrast | $C_{SS} = M_{SS}(T_{2,1}) - M_{SS}(T_{2,2})$ | $C = M(T_{2,1}) - M(T_{2,2})$ |
| Optimal α | 60° | 180° |
| Contrast | .0059 $M_0$ | .0223 $M_0$ |
| Scan Time | 1.28 s | 3.6 s |

TABLE 3-continued

|  | Steady State | Non-Steady State |
|---|---|---|
| CNR Efficiency | 1 | 2.25 |
| SNR Efficiency | 1 | 1.66 |

Because SAR is a concern in fast imaging sequences, shown in Table 4, below, is how contrast and SAR reduce with decreases in Flip Angle. CNR Efficiency vs. Steady State compares the CNR from a non-steady state acquisition with the given flip angle against CNR from a steady state acquisition with optimum flip angle (~60°) for CNR in the steady state.

TABLE 4

| Flip Angle ($\alpha$) | Contrast vs. 180° | CNR Efficiency vs. Steady State | SAR |
|---|---|---|---|
| 180° | 100% | 121% | 100% |
| 150° | 96% | 116% | 69% |
| 120° | 86% | 104% | 44% |

Animal Studies.

To demonstrate detection of $H_2^{17}O$ in vivo, $^{17}O_2$ gas was delivered to a pig during imaging (data not shown). Signal decreases demonstrate the detection of $^{17}O_2$ conversion to $H_2^{17}O$. To demonstrate pulsed delivery of $^{17}O_2$ gas, 1 breath of 40% was delivered to three pigs either as one breath or diluted with nitrogen to simulate room air. A consistent signal drop is observed after each delivery. Because only one breath of gas is used to show change, this represents the smallest volume delivery of gas published.

Figure 14:
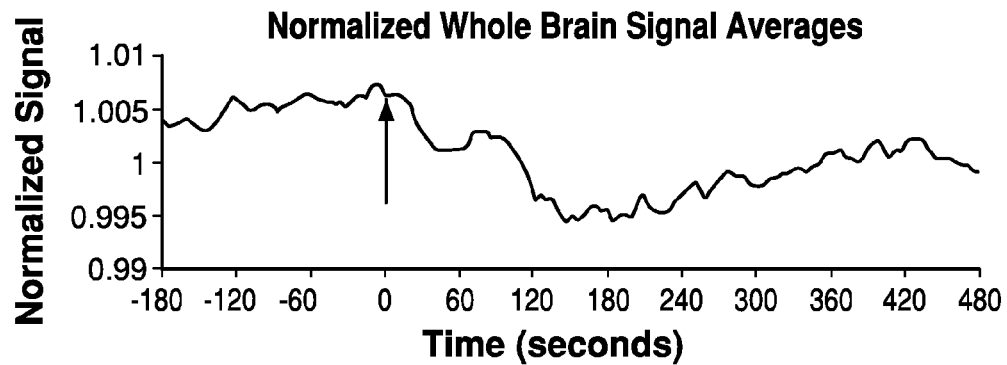
FIG. 14 provides the results of three experiments that were performed with 40% $^{17}O$ and with TSL=200 ms to develop a higher percent signal change, but also with SNR about 40:1 as opposed to 150:1 at TSL=75 ms; the average of the three experiments is depicted as a whole brain signal trace.

Three experiments were performed with 40% $^{17}O$ and their results are pooled. These were performed with TSL=200 ms to develop a higher percent signal change, but with SNR about 40:1 as opposed to 150:1 at TSL=75 ms. Results are shown in FIG. 14. The whole brain signal trace is an average of these three experiments, though ROIs from different regions show similar kinetics. Two pigs were imaged with a protocol of 5 minutes of 100% $O_2$, 2 breaths of 40% $^{17}O$ enriched $O_2$, then 5 minutes of 100% $O_2$. The third pig was imaged with 5 minute room air then 2 breaths of 20% $O_2$ (40% enriched $^{17}O_2$) mixed with 80% $N_2$. The start of $^{17}O_2$ is indicated by the arrow. Because the normalized signal trace from the third experiment is so similar, it has been pooled. Signal changes are statistically significant when compared to baseline (data not shown).

In conclusion, the present study provides many of the technical details of and proof of concept for improvements in indirect detection of $H_2^{17}O$ by $T_{1\rho}$ on clinical scanners, including its use for the clinical in vivo imaging of metabolism.

Although several examples of the present invention have been described, it will be understood by those of skill in the art that the procedures and materials are not limited to those explicitly mentioned. Modifications on the procedures and materials are within the scope and spirit of the present invention.

What is claimed:

1. A method of administering $^{17}O_2$ to a patient for magnetic resonance imaging a region of interest remote from the patient's lungs, comprising:
    providing $^{16}O_2$ to the patient by inhalation;
    a ventilator applying a pulse of $^{17}O_2$ by inhalation comprising an approximately step increase in $^{17}O_2$, a duration of said pulse selected so as to be shorter than a diffusion time lag of metabolized $H_2^{17}O$ in the patient from the patient's lungs to the region of interest; and
    imaging the region of interest during the duration of said pulse.

2. The method of claim 1, wherein the pulse of $^{17}O_2$ has a duration in a range of from about 30 seconds to about 60 seconds.

3. The method of claim 1, wherein the region of interest is the brain, comprising the further step of calculating, using a processor, cerebral metabolic rate of oxygen consumption ($CMRO_2$) from the amount of $^{17}O_2$ measured in an image taken during the imaging step by calculating:

$$CMRO_2 = k_1(dC_b(t)/dt)/C_a(t)$$

where $C_a(t)$ and $C_b(t)$ are the $^{17}O_2$ concentrations in arterial blood as a function of time at times a and b, and $k_1$ is a conversion constant.

4. The method of claim 1, further comprising recovering unused $^{17}O_2$ exhaled by the patient.

5. The method of claim 1, comprising the further step of assisting exhalation by the patient using a pump.

6. The method of claim 5, comprising the further step of monitoring the pressure of exhaled gases and adjusting an exhalation speed of said pump so as to adjust the exhalation pressure to a target exhalation pressure.

7. A ventilation apparatus, comprising:
    means for selecting either a source of $^{16}O_2$ or $^{17}O_2$;
    an inhalation pump for pumping the selected source to a patient at a first pressure;
    an exhalation pump for pumping exhaled gases at a second pressure; and
    means for controlling said selecting means so as to apply a pulse of $^{17}O_2$ to the patient,
    said pulse comprising an approximately step increase in $^{17}O_2$ for a duration selected by the means for controlling said selecting means so as to be shorter than a diffusion time lag of metabolized $H_2^{17}O$ in the patient from the patient's lungs to a region of interest in the patient's body, said region of interest being remote from the patient's lungs.

8. The apparatus of claim 7, wherein the pulse of $^{17}O_2$ has a duration in a range of from about 30 seconds to about 60 seconds.

9. The apparatus of claim 7, wherein the selecting means comprises a valve.

10. The apparatus of claim 7, further comprising means for recovering unused $^{17}O_2$ exhaled by the patient.

11. The apparatus of claim 10, wherein said recovering means comprises a sampling bag that receives exhaled gases output by said exhalation pump and a $CO_2$ absorber that removes $CO_2$ from the exhaled gases before the exhaled gases reach said sampling bag.

12. The apparatus of claim 7, further comprising a pressure transducer that monitors the second pressure and adjusts an exhalation speed of said exhalation pump so as to adjust the second pressure to a target exhalation pressure.

* * * * *

UNITED STATES PATENT AND TRADEMARK OFFICE
CERTIFICATE OF CORRECTION

PATENT NO.       : 8,554,305 B2                                         Page 1 of 1
APPLICATION NO.  : 12/669854
DATED            : October 8, 2013
INVENTOR(S)      : Tailor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 775 days.

Signed and Sealed this
Fifteenth Day of September, 2015

Michelle K. Lee
*Director of the United States Patent and Trademark Office*